United States Patent [19]

Borg

[11] Patent Number: 5,447,959
[45] Date of Patent: Sep. 5, 1995

[54] METHOD OF USING DERIVATIVES OF LONG CHAIN FATTY ALCOHOLS TO TREAT NEURONAL DEGRADATION

[75] Inventor: Jacques Borg, Bischheim, France

[73] Assignee: Medafor, Strasbourg, France

[21] Appl. No.: 27,034

[22] Filed: Mar. 5, 1993

Related U.S. Application Data

[63] Continuation of Ser. No. 720,816, filed as PCT/FR90/00742, Oct. 5, 1990, Pat. No. 5,243,094.

[30] Foreign Application Priority Data

Oct. 13, 1989 [FR] France .................. 89 13456
Feb. 14, 1990 [FR] France .................. 90 01771

[51] Int. Cl.⁶ .................. A61K 31/045; A61K 31/12; A61K 31/075; A61K 31/11
[52] U.S. Cl. .................. 514/725; 514/690; 514/693; 514/703; 514/715; 514/763
[58] Field of Search .......... 514/763, 715, 725, 690, 514/693, 703

[56] References Cited

U.S. PATENT DOCUMENTS

| | | | |
|---|---|---|---|
| 3,689,667 | 9/1972 | Lee | 424/318 |
| 4,034,114 | 7/1977 | Yu et al. | 424/333 |
| 4,092,366 | 5/1978 | Oroshnik | 568/824 |
| 4,687,783 | 8/1987 | Hörrmann | 514/693 |
| 4,889,847 | 12/1989 | Kligman et al. | 514/171 |

FOREIGN PATENT DOCUMENTS

| | | |
|---|---|---|
| 2551914 | 6/1977 | Germany . |
| 2459985 | 2/1979 | Germany . |
| WO84/01899 | 3/1984 | WIPO . |

OTHER PUBLICATIONS

*H-E-B One Daily & Iron Multiple Vitamins & Iron*, (distributed by H.E.B. Food Stores, Corpus Christi, Texas 78469).
Vitamin A, No. 9666, *The Merck Index*, 9th Ed., (1976).
Ehrlich et al., *Chemical Abstracts*, vol. 75, Abstract No. 61125q, p. 230 (1971).
Auperin et al., *Chemical Abstracts*, vol. 93, Abstract No. 93: 61142q, p. 44 (1980).
Das et al., *Chemical Abstracts*, vol. 94, Abstract No. 94: 175328f, p. 753, (1981).
Mozsik et al., *Chemical Abstracts*, vol. 100, Abstract No. 100: 155572v, p. 449 (1984).
Das et al., *Chemical Abstracts*, vol. 101, Abstract No. 101: 38706b, p. 534 (1984).
Kamisaka et al., *Chem. Abs.*, vol. 111, Abs. No. 239327i, pp. 401–402 (1989).
Smith et al., *Chem. Abs.*, vol. 102, Abs. No. 202995p, p. 517 (1985).

*Primary Examiner*—James H. Reamer
*Assistant Examiner*—Michael B. Hydorn
*Attorney, Agent, or Firm*—Merchant, Gould, Smith, Edell, Welter & Schmidt

[57] ABSTRACT

Derivatives of long-chain fatty alcohols, and methods of obtaining them, are provided, as well as pharmaceutical compositions containing derivatives and their uses, in particular in treating or preventing neuro-degenerative illnesses, conditions linked to skin ageing, the phenomena of thrombosis and atherosclerosis, and immune deficiencies.

4 Claims, 2 Drawing Sheets

METHOD OF USING DERIVATIVES OF LONG CHAIN FATTY ALCOHOLS TO TREAT NEURONAL DEGRADATION

This is a continuation of application Ser. No. 07/720,816, filed as PCT/FR90/00742, Oct. 5, 1990, now U.S. Pat. No. 5,243,094.

The present invention relates to derivatives of long chain hydrocarbon fatty alcohols as well as pharmaceutical compositions containing these derivatives, and the use of the latter, in particular as cytotrophic and cytoprotective medicines.

It is generally admitted that the nervous tissue of adult mammals cannot be regenerated following a lesion. This lack of the capacity to regenerate itself may be due to a failure of signals capable of inducing regeneration or to an irreversible lesion which leads to neuronal death (A. J. AGUAYO, in: A. BIGNAMI, F. E. BLOOM, C. L. BOLIS and A. ADELOYE eds, CNS Plasticity and Repair, Raven Press (New York) (1985) pp 31-40). However, neuronal death may be prevented by protecting the nervous tissue from the consequences of ischemia or by providing it with a favourable microenvironment, in particular of neurotrophic or neuroprotective substances; these substances might also promote regeneration of the nervous tissue if they are administered before death occurs.

The neurotrophic factors are agents capable of promoting the survival of neurons and of stimulating neuronal differentiation (J. R. PEREZ-POLO, in J. E. BOTTENSTEIN and G. SATO eds, Cell Culture in the Neurosciences, Plenum Publishing Corp. (1985) pp 95-123). The activation of cellular metabolism may result in the formation of a network of axons oriented towards the target to be innervated. The demonstration of neurotrophic factors may be made in vitro with the aid of cultures of nerve cells (G. BARBIN, I. SELAK, M. MANTHORPE, and S. VARON; NEUROSCIENCE 12: 33-43 (1984)). Cultures of dissociated cells from various regions of the central nervous system (CNS) have made it possible to show the effect of these neurotrophic factors on the survival of the neurons and on their maturation.

Moreover, an experimental lesion to the median septum in the rat leads to a considerable loss of cholinergic neurons (D. M. ARMSTRONG et al., COMP. NEUROL. 264: 421-436 (1987); F. H. GAGE et al., BRAIN RES. 268: 27-37 (1983)). Certain diseases such as Alzheimer's or Parkinson's disease, Huntington's chorea or amyotrophic lateral sclerosis are the consequence of the progressive disappearance of certain neurons (J. T. COYLE et al., SCIENCE, 219: 1184-1190 (1983); J. B. MARTIN, NEUROLOGY 34: 1059-1072 (1984); M. D. YAHR and K. J. BREGMANN, NEUROLOGY vol., Raven Press (New York) (1985)). Some studies have suggested that this loss of neurons could be prevented by the administration by the intracerebroventricular route of neurotrophic factors such as NGF (Nerve Growth Factor) or FGF (Fibroplast Growth Factor) (L. F. KROMER, Science 235: 214-216 (1987); K. J. ANDERSON et al., Nature 332-360-361 (1988); T. HAGG et al., Exp. Neurol. 101: 303-312 (1988)).

Neuronal death may also be linked to the presence of neurotoxic substances. Certain excitatory amino acids have an excitotoxic action on the neurons; when they are injected into the brain of rats, they cause degeneration of certain zones (J. T. COYLE and R. SCHWARCZ, in: Handbook of Chemical Neuroanatomy, Elsevier, Amsterdam (1983) pp 508-527). This phenomenon is similar to that of the neuronal degeneration observed in the hippocampal area in man and which is called hippocampal sclerosis (Meldrum, Clin. Sci 68: 112-113 (1985). This type of lesion may be reproduced by intracerebral injections of excitotoxic substances, such as ibotenic acid. It has been suggested that the loss of hippocampal neurons which is observed in Alzheimer's disease and subsequent to a cerebral ischemia might be linked to the high density of glutamate receptors present on these neurons (S. M. ROTHMANN and J. W. OLNEY, Ann. Neurol.; 19: 105-111 (1986)). Neurotoxic amino acids may also induce lesions at a distance by the intermediary of glutamatergic projections and which resemble the lesions observed in epilepsy (J. V. NADLER et al., Nature 271: 676-677 (1978) and in Huntington's chorea (J. T. COYLE and R. SCHWARZCZ, Nature 263: 244-246 (1976)). The excitotoxins might also be implicated in the genesis of ischemic lesions; ischemia increases the extra-cellular concentration of excitatory amino acids causing hyperstimulation, neuronal swelling, followed by cell lysis (Meldrum, Adv. Neurol.; 44: 849-855 (1986); S. M. ROTHMANN and J. W. OLNEY, Ann. Neurol. 19: 105-111 (1986)). Similarly, during epilepsy increased release of neurotransmitter might produce neurodegenerative lesions of the same type (Y. BENARI, Neuroscience 14: 375-403 (1985)).

The inventors have demonstrated that the long chain fatty alcohol n-hexacosanol possesses neurotrophic and neuroprotective activities in vitro. This long chain fatty alcohol has been isolated from the tropical plant *Hygrophila erecta*, Hochr. (Acanthaceae) (Borg et al., Neuroscience Lett. 213: 406-410 (1987)). If it is added at a concentration of 500 nM to fetal rat neurons in culture, it increases axonic growth by a factor of 4 to 6 as well as the number of collaterals, in particular in the case of multipolar neurons. This substance also increases considerably the biochemical differentiation of the neurons in culture: it increases the amount of proteins and doubles the specific activities of two neuronal enzymes, glutaminase activated by phosphate and the neurospecific enolase by 32 and 78%, respectively.

However, the results of the in vitro study of the properties of n-hexacosanol do not make it possible to appraise its possible in vivo activity, in view of the differences existing between the in vitro and in vivo environmental conditions.

Furthermore, n-hexacosanol administered by the peripheral route significantly attenuates neuronal degeneration in the cerebrum after axotomy. It also significantly reduces the loss of neurons following an injection of neurotoxins into the cerebrum. This effect confirms the neurotrophic and neuroprotective properties of n-hexacosanol.

The object of the invention is derivatives of long chain fatty alcohols, derived from terpene compounds, exhibiting potent neurotrophic and neuroprotective properties in vitro and in vivo on various nervous tissues.

These derivatives are capable of crossing the blood brain barrier and have a bioavailability much higher than the other neurotrophic factors presently known.

Advantageously, the derivatives of the invention reach specific cell targets, which makes them therapeutic tools of the greatest importance.

The invention also relates to derivatives of long chain fatty alcohols exhibiting cytotrophic and cytoprotective properties with respect to a large variety of cells of the organism.

The invention relates to derivatives of fatty alcohols corresponding to the following general formula:

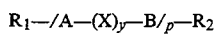

$$R_1\text{—/A—}(X)_y\text{—B/}_p\text{—}R_2$$

in which:
p is equal to 1 or 2,
y = 0 or 1,
A—(X)$_y$—B is a hydrocarbon chain comprising from 7 to 50 carbon atoms, where appropriate substituted by one or more halogen atoms, in particular fluorine, or by one or more alkyl groups of 1 to 3 carbon atoms, or by one or more OR$_a$ groups, R$_a$ representing H or an alkyl group of 1 to 3 carbon atoms, or by one or more oxy (=O) groups, and in which:
  A and B, identical or different, are saturated or unsaturated aliphatic chains.
X is also a sequence comprising a saturated or unsaturated hydrocarbon chain forming part of a cyclic structure, itself saturated or unsaturated, comprising from 1 to 5 rings, in particular of the benzene, pentane and hexane type, these rings being substituted where appropriate by one or more oxy (=O) or OR$_a$ groups R$_a$ having the meaning indicated above, this hydrocarbon chain comprising where appropriate, a carbonyl or oxycarbonyl function,
R$_1$ and R$_2$, identical or different, represent:
  a hydrogen atom,
  a —CN group,
  an amine group of formula —NR'$_1$R'$_2$ in which R'$_1$ and R'$_2$, identical or different represent H or an alkyl group of 1 to 3 carbon atoms,
  a halogen atom, in particular a fluorine atom,
  a

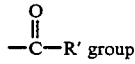

$$\begin{array}{c} O \\ \parallel \\ -C-R' \end{array} \text{ group}$$

in which R' represents a hydrogen atom or an alkyl group of 1 to 5 carbon atoms, and preferably 1 to 3 carbon atoms, or a group of formula OR$_b$, R$_b$ representing an alkyl group of 1 to 3 carbon atoms, or an amine group of formula —NR'$_1$R'$_2$ described above,
  a group of formula (A):

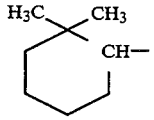

optionally comprising a double bond and being, where appropriate, substituted by one or more halogen atoms, in particular fluorine, or one or more —CH$_3$ and/or —OH and/or —OR groups, R being as defined below, and/or a oxy (=O) group,
  a —OR group, in which R represents a hydrogen atom or an alkyl group of 1 to 3 carbon atoms or
  a

$$\begin{array}{c} O \\ \parallel \\ -C-R', \end{array}$$

R' having the meaning indicated above or a derivative of monophosphoric acid of formula:

$$\begin{array}{c} O \\ \parallel \\ -P-OR_3 \\ | \\ O^-Y^+ \end{array}$$

in which Y$^+$ represents a metal ion preferably Na$^+$, K$^+$, NH$^+_4$ and R$_3$ represents
  a hydrogen atom or a halogen atom, in particular fluorine,
  a nucleotide, glucose or galactose,
  an amino acid, a peptide or a protein,
  a metal ion, preferably Na$^+$, K$^+$, NH$^+_4$,
  a hydrocarbon chain of formula R$_1$—/A—(X)$_y$—B/$_p$— or formula —/A—(X)$_y$—B/$_p$—R$_2$ comprising from 7 to 50 carbon atoms, where appropriate, substituted by one or more halogen atoms, in particular fluorine, or by one or more alkyl groups of 1 to 3 carbon atoms, or by one or more OR$_a$ groups, R$_a$ being as defined above or by one or more oxy (=O) groups, and in which A, X, B, R$_1$, R$_2$, y and p have the meanings indicated above, the said derivatives comprising at least one

$$\begin{array}{c} O \\ \parallel \\ -C-R' \end{array}$$

group, a —OR group, a —CN group or a —NR'$_1$R'$_2$ group R'$_1$, R'$_2$, R and R' having the meanings indicated above, provided that:
  when Y = 0 and one of the pair R$_1$ and R$_2$ represents a group of formula (A) whereas the other member of the pair represents H, or R$_1$ and R$_2$ represent a group of formula (A), the chain A—B does not represent an isoprene polymer, and
  when Y = 1, and X represents a cyclic structure of formula:

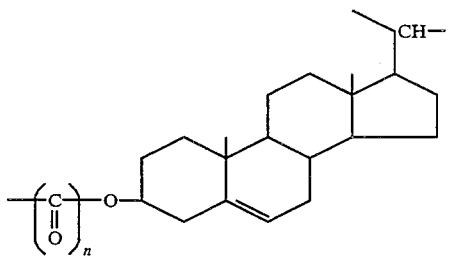

in which n = 0 or 1, and optionally comprising an oxy group at position 7, A and B are hydrocarbon chains of at least 5 carbon atoms,
the derivatives of the following formulae being excluded:
CH$_3$—(CH$_2$)$_n$—CH$_2$ OH in which n varies from 5 to 38, as well as secondary aliphatic alcohols of 7 to 40 carbon atoms, where appropriate substituted by one or several alkyl groups, and comprising where appropriate a double bond, $$H-(CH_2-\underset{CH_3}{C}=CH-CH_2)_n-CH_2-\underset{CH_3}{CH}-CH_2-W$$

in which n varies from 1 to 4, and W represents —CH$_2$OH or —COOR$_a$, R$_a$ having the meaning indicated above, $$CH_3-(CH_2)_{nA}-\underset{R'_A}{C}=\underset{R'_B}{C}-(CH_2)_{nB}-CH_2OH$$

in which
$n_A=7$, $n_B=11$ and $R'_A=R'_B=H$
$n_A=7$, $n_B=11$ and $R'_A=R'_B=Br$
$n_A=n_B=7$ and $R'_A=R'_B=H$
$n_A$ is an integer from 15 to 19, $n_B$ is an integer from 7 to 11, $n_A+n_B=26$ and $R'_A=R'_B=H$ $$R'_1+CH=CH-\underset{CH_3}{C}=CH)_n CH=CH+CH=\underset{CH_3}{C}-CH=CH)_n R'_1$$

in which n varies from 0 to 3 and R'$_1$ represents one of the following groups:

$$H_3C-\underset{CH_3}{C}=CH-(CH_2)_2-\underset{CH_3}{C}=CH-$$

$$H_3C-\underset{\underset{CH_3}{|}}{\overset{OCH_3}{C}}-CH_2-CH=CH-\underset{CH_3}{C}=CH-$$

$$H_3C-\underset{\underset{CH_3}{|}}{\overset{OCH_3}{C}}-(CH_2)_3-\underset{CH_3}{C}=CH-$$

$$H_3C-\underset{\underset{CH_3}{|}}{\overset{OH}{C}}-(CH_2)_3-\underset{CH_3}{C}=CH-$$

$$H_3C-\underset{\underset{CH_3}{|}}{\overset{OCH_3}{C}}-\overset{O}{\overset{\|}{C}}-CH=CH-\underset{CH_3}{C}=CH-$$

$$HO-CH_2-\underset{CH_3}{C}=CH-(CH_2)_2-\underset{CH_3}{C}=CH-$$

When the R$_3$ group of the above-mentioned formula of the derivatives of the invention is a nucleotide or a peptide derivative, it preferably represents:
uracil, cytosine, guanine, adenosine or thymine, in the case of a nucleotide,
the muramylpeptides and -dipeptides, transferrin or insulin when it is a peptide or a protein.

The fluorinated derivatives of the invention are particularly attractive in particular from the point of view of bioavailability and chemical stability.

The invention relates more particularly to the derivatives corresponding to the general formula mentioned above in which p=1 (also designated as monomers in the subsequent description).

One category of preferred derivatives of the invention is represented by the derivatives of formula:

comprising, where appropriate, 1 to 10, and preferably 1 to 5, double bonds and in which R$_2$ represents CN, OR or $$-\overset{O}{\overset{\|}{C}}-R',$$

R and R' having the meanings indicated above and n is an integer varying from 1 to 10. and, more particularly, the saturated and unsaturated analogues of vitamin A (or retinal) corresponding to the following formula:

comprising, where appropriate, 1 to 10, and preferably 1 to 5, double bonds, and in which n is an integer varying from 1 to 10. The molecular weights of the saturated and unsaturated analogues of vitamin A of the invention are of the order of 280 to 447.

Another particularly attractive category of derivatives of the invention is represented by the homologues of squalene (a terpene compound of 30 carbon atoms) corresponding to the following formulae:

comprising, where appropriate, 1 to 10 and 1 to 9 double bonds, respectively, and preferably 1 to 5 double bonds. The molecular weights of the homologues of squalene according to the invention are of the order of 361 to 395.

The practically completely saturated derivatives geranylgeraniol (C25) and geraniol (C20) represent preferred derivatives of the invention. Among the latter, those corresponding to the following formulae are singled out:

comprising, where appropriate, 1 to 5 and 1 to 4 double bonds, respectively. The molecular weights of these derivatives according to the invention are of the order of 240 to 368.

Particularly preferred derivatives of the invention are those in which y=1 and X represents the group of formula:

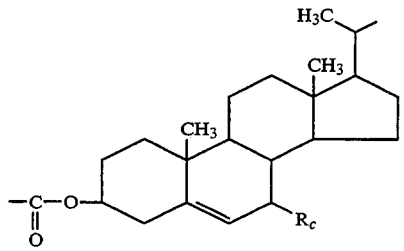

in which Rc is —H or —OH.

The esters of cholesterol of formula:

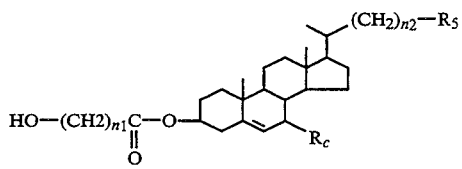

comprising, where appropriate, 1 to 7 double bonds and in which:

Rc and $R_5$, identical or different, represent —H or —OH, $n_1$ and $n_2$ are identical or different integers, varying from 5 to 15, also constitute a preferred class of derivatives of the invention. The molecular weights of the cholesterol derivatives according to the invention are of the order of 445 to 643.

Since the terpenes are by definition polymers of isoprene, a structure with 5 carbon atoms, cholesterol also forms part of the terpenes in as much as its precursor, lanosterol, is a triterpene. The presence of the rings of cholesterol increases the rigidity of the derivatives of the invention, which confers on them improved capacity to integrate into the cell membrane.

The invention relates more particularly also to the dimeric derivatives corresponding to the general formula of the derivatives of the invention in which p=2.

These dimeric derivatives possess a size which enables them to pass right through the cell membrane, thus modifying the physicochemical properties of this membrane, and thus confers on them particularly good activity.

The dimers of the invention comprise 1 to 20, and preferably 1 to 10, double bonds.

Among these derivatives, mention should be made of those of formula:

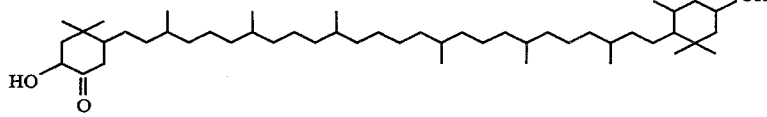

comprising, where appropriate, 1 to 14 double bonds, and preferably 1 to 7 double bonds. The molecular weights of the dimeric compounds according to the invention are of the order of 572 to 914.

The derivatives of the present invention are obtained from terpene substances or from a cyclic structure derived from the terpenes of synthetic or natural origin, having undergone:

either a partial ozonolysis with the aid of ozone, which has the effect of reducing the length of the hydrogen carbon chain of the terpene compound or an addition of one or more —OH functions to one or both extremities of these terpene compounds, in particular according to the method of Wittig with the aid of a diol or an acid alcohol (which will be more particularly developed in the detailed description which follows), or total or partial hydrogenation, or a combination of several of the above-mentioned operations.

The saturated and unsaturated derivatives of vitamin A according to the invention are obtained, in particular, by coupling by means of the Wittig reaction the retinal of formula:

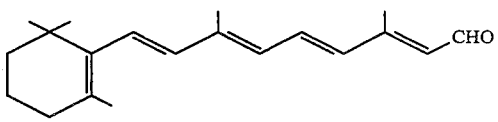

in which an ylid derivative of tetrahydropyran bromide (THP-bromide) of formula:

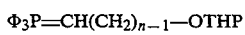

in which n is an integer varying from 1 to 10, this latter substance itself being obtained by reaction of a salt of tetrahydropyran bromide of formula: Br—CH$_2$—(CH$_2$)$_{n-1}$—OTHP (THP=tetrahydropyran) with a triphenylphosphine of formula:

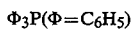

The ylid thus obtained is placed in contact with retinal in the presence of butyllithium which leads to the formation of a derivative of formula:

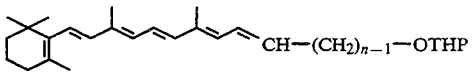

This latter is then hydrogenated for a defined period of time, which leads to the derivative of formula:

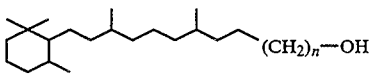

in which n=0 to 10, totally saturated or containing 0 to 10 double bonds as a function of the hydrogenation time.

The squalene derivatives according to the invention are obtained in the following manner. Since squalene, a terpene derivative of 30 carbon atoms, is too large to have good biological activity, the terminal double bonds of this latter are cleaved by partial ozonolysis, in particular for 2 hours. Then a hydroxyl function is introduced at one or other or at both extremities of the derivative thus obtained, in particular according to the method of Wittig previously described. The derivative is then hydrogenated for a defined period of time in order to lead to a final derivative totally saturated or containing from 0 to 10 double bonds.

The geranylgeraniol and geraniol derivatives are obtained in particular according to a synthetic process identical with that used for the derivatives of vitamin A mentioned above, namely the Wittig method to lengthen the chain and introduce one or two hydroxyl functions at the extremities of the said hydrocarbon chain of geranylgeraniol or geraniol, the formulae of which are the following:

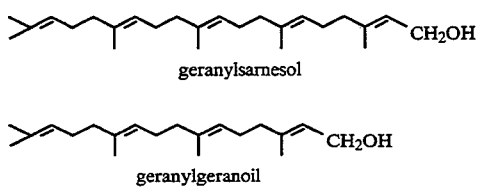

geranylsarnesol geranylgeranoil followed by hydrogenation which gives rise to practically saturated derivatives.

The cholesterol derivatives of the invention are obtained by formation of an ester linkage between the hydroxyl at $C_3$ of cholesterol of formula:

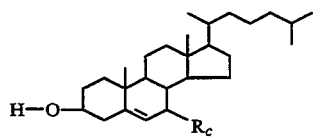

in which $R_c$ has the meaning indicated above, and an acid alcohol of formula

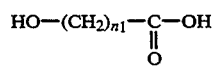

in which $n_1$ has the meaning indicated above, which leads to the formation of a cholesterol derivative, the formula of which is indicated below:

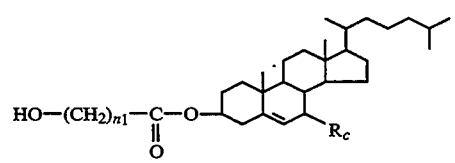

The cholesterol derivative of the invention of formula:

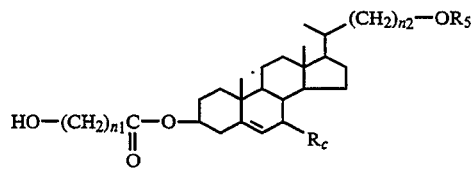

comprising, where appropriate, 1 to 14 double bonds and in which $n_1$, $N_2$, $R_c$ and $R_5$ have the meanings indicated above, is obtained according to the Wittig method previously described carried out on pregnenolone which contains a hydroxyl function or function of the $-OR_5$ type ($R_5$ having the meaning indicated above) at the end of the chain.

The dimeric compounds of the invention are obtained either from compounds treated in an identical manner with that described above for the monomers of the invention (for example natural carotenoids of various sources or synthetic carotenoids containing 40 to 60 carbon atoms, and which are linear or possess one ring in their structure), or by coupling of two monomeric units, in particular by hydrogenation on Pd/C in ethanol.

Since the previously described fatty alcohol derivatives of the invention are only slightly soluble in aqueous media, their use for biological studies or for therapeutic uses may present methodological difficulties. In order to solve this problem, water-soluble prodrugs represented by the monophosphoric acid esters were synthesized. These compounds are hydrolysed in the organism to give the starting materials, namely the derivatives of the invention for which R=H.

These compounds are particularly water-soluble (more than 10% in water, depending on the derivatives), hence the solutions obtained are compatible with intravenous injection. They improve the bioavailability of the derivatives of the invention which makes it possible to potentiate the biological effects observed. Thus the presence of the phosphate group has made it possible to administer an aqueous solution of corticosteroids without loss of biological activity (R. J. W. CRELYN and I. Khattak, Chemistry of steroid phosphates. Phosphorus 27 (1976) 237-246).

The radical represented by $R_3$ makes possible a better targetting of the derivative of the invention. It may promote the penetration of the derivative across the membranes (bacterial membrane) or the diffusion from the capillaries of the digestive tract, the meningeal membrane or other tissues (F. IGLESIAS-GUERRA, J. M. NEUMANN and T. HUYNH-DINH, Synthetic 6-glutamatecosyl phospholipid as a drug transport system/Tetrahedron Lett. 28 (1987) 3581-3584). This radical also enables the derivative to be bound to a specific receptor: hence, the derivative will act specifically on the cells which exhibit such a receptor. Similar reasoning has led to the synthesis of the phosphate derivatives of certain steroid hormones (L. LEBEAU, C. MIOSKOWSKI and P. OUDET, Synthesis of phospholipids linked to steroid hormone derivatives. Chemistry and Physics of Lipids, 46 (1988) 57-62).

The water-soluble derivatives of the invention for which R represents the group

in which $R_3$ and $y^+$ are as defined above, are obtained by phosphorylation of a monomeric or dimeric derivative of the invention for which $R=H$, with o-phenylene phosphochloridate, or with the bi-phosphochloridate followed by oxidative hydrolysis, in particular by means of lead tetraacetate.

The operating conditions for all of the reactions described above will be developed more particularly in the detailed description which follows:

The derivatives of the invention promote nerve regeneration and have a neuroprotective effect; in particular, they exhibit the following properties:

They increase the extension of axons in vitro and in vivo, and facilitate repair following traumatic lesions to the CNS and PNS (peripheral nervous system) by promoting the extension of axons and the formation of new cell contacts and, hence, functional recovery. They attenuate the effect of ischemia, promote neuronal survival and reduce wallerian degeneration after a lesion.

They protect the neurons from cell death subsequent to exposure to neurotoxic substances, such as heavy metals or neuroexcitatory substances, such as glutamate and its analogues.

The derivatives of the invention are cytotrophic factors, in particular for the cells of the skin and the endothelial cells. They promote the repair of lesions of some cell layers such as the cells of the skin or the cells of the vascular endothelium. These derivatives enhance the differentiation of the cells of the dermis, epidermis or the endothelial cells; they increase the formation of extensions and the repair of the lesion by the cells which surround it.

The derivatives of the invention have a cytoprotective effect which is exerted, in particular, on hepatic cells, cardiac striated muscle cells and renal glomerular cells. They protect these cells against chemical lesions or lesions associated with an ischemia. These derivatives also make it possible to protect cardiac tissue against the consequences of an interruption of blood flow, in particular in the coronary arteries. The derivatives of the invention thus make it possible to protect hepatic cells, renal cells and cardiac muscle cells against degeneration of chemical or ischemic origin.

The derivatives of the invention also exhibit a trophic effect on the cells of the renal glomerulus. They lead to an improved synthesis and the secretion of fibrinolytic factors such as the plasminogen activators. Hence, they promote fibrinolysis and inhibit the formation of thrombi, in particular subsequent to acute or chronic renal diseases, glomerulonephrites or intra-vascular coagulation.

The derivatives of the invention have a cytotrophic effect on the cells which participate in the immune defenses of the organism, in particular the macrophages, the monocytes and the lymphocytes. These derivatives promote the differentiation of the lymphocytes, macrophages and monocytes; they enhance the production of the factors of immunity, promote the acquisition of differentiated characters and reinforce the natural or induced immune defenses.

The derivatives of the invention have a cytotrophic effect on the mastocytes and basophilic leucocytes which play an essential role in inflammatory phenomena. These derivatives promote the acquisition of differentiated characters of these cells, modify their response to stimulation by an antigen and by the IgE and diminish the subsequent production of histamine. They also modify the response of smooth muscle cells to the mediators of inflammation, such as histamine, the leucotrienes and the prostaglandins.

The derivatives of the invention have a cytotrophic and differentiating effect on cells which participate in the defense of the organism against neoplasia. They enhance the phagocytic activity of the macrophages, lymphocytes and monocytes and increase the secretion of tumoricidal factors, such as the TNF (tumor necrosis factor). They also have a differentiating effect on cancerous or precancerous cells, such as the promyelocytes.

The derivatives of the invention also have a bacteriostatic effect. They inhibit bacterial proliferation, in particular that of the Gram+ bacteria and the mycoplasmas. When the derivatives of the invention are added to a culture containing Gram+ bacteria, as for example Streptococcus mutans, Clostridium butyricum or Streptococcus sanguis or mycoplasmas such as Mycoplasma pneumoniae or Mycoplasma gallisepticum, a slowing of their proliferation is observed which can be measured by the time course of the change of turbidity of the culture medium, or by the variation of pH of the medium. It is noticed that in the culture containing long chain fatty alcohols of the invention, the increase in the optical density is markedly slowed down compared with the control medium as is the acidification of the medium.

The important role of these compounds is confirmed by the fact that the inhibition of their synthesis in Clostridium butyricum leads to a significant slowing down of growth (GILBERTSON et al., J. Lipid. Res., 19 (1978) 757-762). Furthermore, the presence of long chain fatty alcohols of the invention in the medium is likely to promote the bactericidal action of certain antibiotics. Thus, the combination of tridecanol and gentamycin leads to inhibition of the growth of Streptococcus mutans (GILBERTSON et al., Antimicrob. Agents Chemother., 26 (1984) 306-309).

Furthermore, the derivatives of the invention possess an anti-vital action which is exerted mainly on the viruses possessing an envelope such as the herpes virus, VSV (Vesicular stomatitis virus), the rabies virus, the viruses of the HIV type (virus responsible for AIDS). The experimental model making it possible to demonstrate the anti-vital activity of the fatty alcohols according to the invention varies with the virus under study. It is a matter of selecting the cell types sensitive to the virus under study; hence, fibroblasts, renal cells, erythrocytes or neurons should be selected.

In all cases, an inhibition of the cytopathogenic effect of the virus is observed when fatty alcohols of the invention are added to the culture medium. This effect is measured by means of biochemical or morphological criteria of cellular degeneration. It is noted that at the same infectious dose, the cells in culture are appreciably more resistant to the virus when the medium contains long chain fatty alcohols of the invention. The anti-vital action may be exerted either directly at the level of the replication of the virus within the cell or by a mechanism of inactivation which diminishes the infectious properties of the virus (SNIPES et al., Antimicrob. Agents Chemother., 11 (1977) 98–104).

The invention also relates to the pharmaceutical compositions containing at least one of the above-mentioned derivatives in combination with a physiologically acceptable vehicle, and the use of these compositions, in particular in the following areas of treatment:

(a) the treatment or the prevention of neuronal degeneration in particular during the course of neurodegenerative diseases and neuronal loss associated with chemical substances or excitatory amino acids such as glutamic acid, (b) the treatment or prevention of lesions to nervous tissue in mammals whether they be traumatic lesions, chemical lesions, lesions due to a disease or a congenital deficiency, (c) the treatment of Alzheimer's or Parkinson's disease, Huntington's chorea and other neurodegenerative diseases, epilepsy, wallerian degeneration, cerebral ageing and genetic diseases such as the Down syndrome, (d) the treatment and prevention of the cerebral lesions associated with neurosurgery (these compositions being administered concomitantly with surgery), (e) the healing of cutaneous lesions as well as the treatment and prevention of the phenomena associated with skin ageing, (f) the repair of vascular lesions (of traumatic or chemical origin) as well as the treatment and the prevention of the phenomena associated with thrombosis and atherosclerosis, (g) the treatment and prevention of the degeneration of hepatic, renal or cardiac tissue, in particular when it is due to chemical or medicamentous substances which are toxic for these organs, (h) the treatment and prevention of gastric or duodenal ulcers, (i) the treatment of acquired or heredity immune deficiencies, and the stimulation of the immune defenses, in particular at the level of the central nervous system, in particular by activation of the macrophages and the lymphocytes, (j) the treatment of inflammatory and acute allergic processes such as asthma, allergic rhinitis, anaphylactic shock or urticaria, (k) the treatment and prevention of neoplasia and tumors such as hepatic tumors or bone tumors, and the prevention of the propagation of metastases derived from cancerous tumors, (l) the treatment and prevention of all of the diseases associated with Gram+ bacteria and the mycoplasmas, in particular pulmonary urogenital and buccal infections, (m) to promote the grafting of nerve tissues of fetal or adult origin, or the grafting of placenta or pancreatic tissues or cells with an immune function, (n) the treatment and prevention of the diseases associated with viruses possessing an envelope such as herpes, rabies and AIDS.

The invention also relates to the use of a derivative of formula:

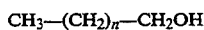

$$CH_3-(CH_2)_n-CH_2OH$$

in which n varies from 5 to 38, or is a secondary aliphatic alcohol of 7 to 40 carbon atoms, where appropriate substituted by one or more alkyl groups, and containing where appropiate one double bond in order to obtain a medicine for:

(a) the healing of cutaneous lesions as well as the treatment and prevention of the phenomena associated with skin ageing, (b) the repair of vascular lesions (of traumatic or chemical origin) as well as the treatment and prevention of the phenomena associated with thrombosis and atherosclerosis, (c) the treatment and prevention of the degeneration of hepatic, renal or cardiac tissue, in particular when it is due to chemical or medicamentous substances which are toxic for these organs, (d) the treatment and prevention of gastric and duodenal ulcers, (e) the treatment of acquired or hereditary immune deficiencies, and the stimulation of the immune defenses, in particular at the level of the central nervous system, in particular by activation of the macrophages and the lymphocytes, (f) the treatment of inflammatory and acute allergic processes, such as asthma, allergic rhinitis, anaphylactic shock or urticaria, (g) the treatment and prevention of neoplasia and tumors, such as hepatic tumors or bone tumors, and the prevention of the propagation of metastases derived from cancerous tumors, (h) the treatment and prevention of all of the diseases associated with Gram+ bacteria and the mycoplasmas, in particular pulmonary, urogenital and buccal infections, (i) to promote the grafting of nervous tissue of fetal or adult origin, or the grafting of placenta or pancreatic tissues, or of cells with an immune function.

Advantageously, the treatment of the diseases and disorders mentioned above with the derivatives of the invention as neurotrophic and neuroprotective substances is carried out in combination with the use of grafts of nervous tissue at the site of the lesion, in particular grafts of nervous tissue of fetal or adult origin, or grafts of placenta or pancreatic tissue (treatment of diabetes) or also of cells with an immune function (treatment of cancers, in particular cancer of the kidney).

This combination makes it possible to promote the functional recovery or to protect the nervous tissue by various mechanisms such as: a trophic effect on the nervous tissue; the release of neurotransmitters or hormones; or the re-innervation of certain elements of the nervous tissue. It is also possible to associate this combination of nerve grafts and derivatives of the invention with grafts of glial cells or tissue capable of producing neurotrophic factors (such as the neuronal growth factor (NGF), or the fibroblast growth factor (FGF), the platelet-derived growth factor (PDGF), the insulin-like growth factor (IGF or somatomedins).

The above-mentioned pharmaceutical compositions preferably comprise efficacious doses of derivatives of the invention which are of the order of 0.01 mg/kg to 100 mg/kg, and in particular from 0.5 mg/kg to 10 mg/kg.

Pharmaceutical compositions of the invention advantageously comprise a single dose included between 0.5 mg and 500 mg of the derivative of the invention in combination with a vehicle or pharmaceutically acceptable excipient, in particular for the parenteral or oral routes.

The optimal concentration of these molecules varies according to the magnitude of the lesion or the existance of secondary effects.

The pharmaceutical compositions of the invention are administered by the parenteral route, in particular by the intravenous, intramuscular, intracerebral or intraperitoneal route; they are also administered by the sublingual or vaginal route or by means of implants or pumps.

The pharmaceutical compositions of the invention are preferably administered by the oral route.

The parenteral preparations are prepared by sterilization through a filter with 0.22 μm pores; sterilely stoppered 1 ml vials are prepared containing 100 mg of these molecules. It is also possible to use a lyophilisate which is reconstituted before intravenous injection.

The compositions of the invention suitable for the oral route are advantageously available in the form of pills, gelatin capsules, suspensions, powders, emulsions or capsules.

Advantageously, the above-mentioned pharmaceutical compositions used in the field of neuroprotection comprise at least one derivative of the invention in combination with other neurotrophic or neuroprotective factors, such as the NGF, the FGF, the somatomedins, the benzodiazepines, antagonists of the kappa receptors, calcium channel blockers, and antagonists of the receptors of the excitatory amino acids.

Particularly useful pharmaceutical compositions in the context of cell grafts, in particular neuronal grafts, contain one or more derivatives of the invention in combination with cells having the properties of those originally contained in the part(s) containing the lesion where the graft has to be performed. As an example, such pharmaceutical compositions according to the invention are available in the form of injectable solutions containing a defined amount of one or more of the derivatives of the invention in combination with cells derived from the septum or hippocampus (these cells being taken from an organism other than the one receiving the grafts).

In the context of their bacteriostatic use, particularly useful pharmaceutical compositions contain one or several derivatives of the invention in combination with one or several antibiotics.

All of the pharmaceutical compositions of the invention are designed for the treatment and/or the prevention of the diseases described above in mammals.

The invention also relates to culture medium containing at least one of the compounds of the invention in combination with products suitable for the culture of cells. These culture media are designed more particularly for the culture of cells such as human or animal cells derived from embryonic dissociated tissue of the newborn, adult or old animal tissue. The derivatives of the invention promote the survival and differentiation of these tissues in vitro. As examples of cells likely to be placed in culture in the media of the invention, mention may be made of: neurons, macrophages, hepatocytes, renal cells, fibroblasts, endothelial cells, lymphocytes and bone marrow cells. These cells may be administered to a patient for a therapeutic purpose, possibly after having undergone an in vitro treatment with one or more derivatives of the invention in the above-mentioned culture medium.

As an example, the invention also relates to pharmaceutical compositions containing cells such as those indicated above in combination with a pharmaceutically acceptable vehicle, the cells being derived from a cell culture according to the invention, the cells being preferably free of other constituents of these culture media.

As illustrations, examples of the culture media of the invention are more particularly described in the detailed description which follows.

Other characteristics of the invention will also become apparent during the course of the description which follows of examples of the synthesis and biological properties of the derivatives of the invention. It will be obvious that these examples are not in any way limiting.

I EXAMPLES OF THE SYNTHESIS OF THE DERIVATIVES OF THE INVENTION

1) Saturated and unsaturated derivatives of vitamin A
Example A:
a) Preparation of the phosphonium bromide salt In order to avoid side reactions, the bromides of suitable long chain primary alcohols $Br(CH_2)_n$—OH are treated with 4-methoxy 3,4-dihydropyran in order to protect the primary hydroxyl.

The phosphonium bromide salt is prepared by the addition of 0.4 moles of triphenylphosphine to a solution of 0.4 moles of methoxytetrahydropyran bromide in 100 ml of toluene.

The solution is then heated at 60° C. overnight. The phosphonium bromide salt precipitates on cooling, it is filtered off and washed with 100 nil of toluene.

b) Wittig reaction 0.8 ml (1.26 mmoles) of n-butyllithium (hexane) is added dropwise to a suspension of 2 mmoles of the phosphonium bromide salt obtained in the manner indicated above in 9 ml of anhydrous hexane; the reaction is allowed to proceed at room temperature overnight.

0.6 mmoles of retinal dissolved in 2 ml of hexane are then added dropwise. After a reaction time of 1 hour, the mixture is cooled in an icebath and filtered to remove the triphenyl phosphine oxide formed. After evaporation of the solvent, the olefin formed is isolated in a yield of 80%.

The olefin (0.5 mmoles) dissolved in 30 ml of methanol is hydrogenated in the presence of 50 mg of 5% palladium on charcoal (Pd/c). The desired product linked to methoxytetrahydropyran is obtained in quantitative yield. The protecting group is removed by a simple treatment with a solution of 0.1N HCl.

The number of double bonds hydrogenated is determined by the duration of the reaction. It is also possible to protect some of the double bonds which are not required to be saturated in particular by the method of protection as the dibromide. Example B: elongation of the chain by one, two or three carbon atoms starting from perhydrogenated retinol:

B-I Perhydrogenated retinol + one carbon atom
1. Reaction:

METHOD OF SYNTHESIS (1)

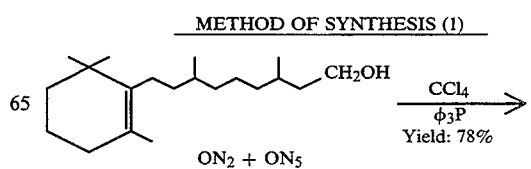

$ON_2 + ON_5$

-continued
METHOD OF SYNTHESIS (1)

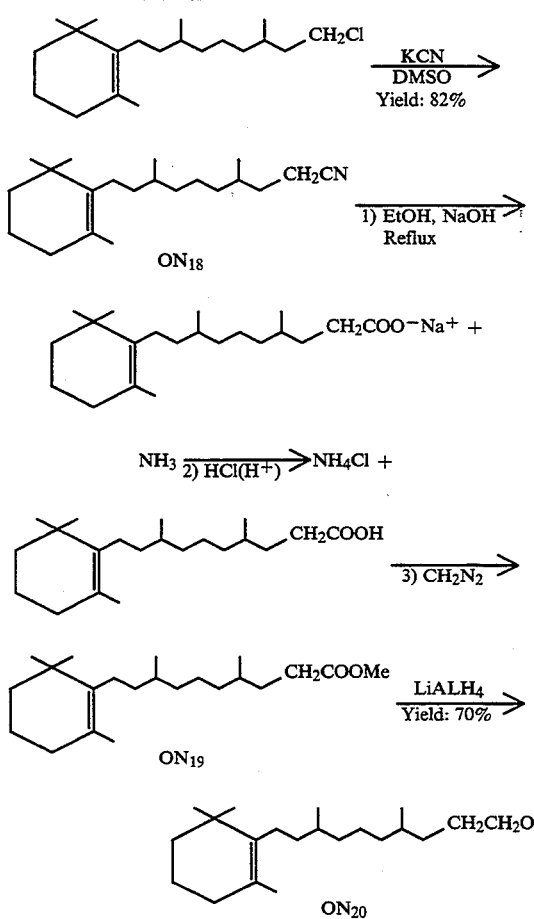

1), 2) and 3) are carried out directly without purification.

2. Procedure:
a. Chlorination

Anhydrous reaction, $CCl_4$ distilled from $P_2O_5$. The perhydrogenated retinol (200 mg) dissolved in 20 ml of $CCl_4$ is placed in a round-bottomed flask. $\Phi_3P$ is then added in slight excess. The reaction is allowed to proceed with stirring under argon and under reflux at 85° C. Reaction time: 24 hours. The round-bottomed flask is then placed in ice-water so that the $\Phi_3P=O$ precipitates. $\Phi_3P=O$ is then removed by filtration.

b. Synthesis of the nitrile

Anhydrous reaction. DMSO distilled from $CaH_2$ in a vacuum, KCN (2 equivalents)+DMSO (20 ml) are placed in a round-bottomed flask. The mixture is heated under argon at 100° C. until the dissolution of KCN is complete. A solution of chloride ($4\times10^{-3}$ moles) previously prepared in 5 ml of DMSO is then added. The temperature is raised to 120° C. Reaction time: 6 hours. Saturated NaCl+ether are then added and the mixture is extracted with ether; the extract is washed with water.

c. Synthesis of the ester

The nitrile ($3\times10^{-3}$ moles) dissolved in 15 ml of ethanol+5 ml of a 12N solution of NaOH are placed in a round-bottomed flask. Reaction is allowed to proceed with stirring under argon at reflux overnight. The EtOH is evaporated and the residue is diluted with $H_2O$ and the impurities are extracted with ether. Concentrated HCl is added dropwise to the aqueous phase until the pH=2. The aqueous phase is extracted with ether and the organic phase is washed with $NaCl+H_2O$. Then the ether is evaporated. The residue is dissolved in ether and an ethereal solution of $CH_2N_2$ is added dropwise with stirring to the solution cooled in an ice-water bath. Concentrated acetic acid is added to destroy the excess $CH_2N_2$ once reaction is complete (check by means of TLC). The reaction solution is washed with NaCl. Total reaction time: 10 hours. Total yield: 90%.

d. Reduction of the ester to the alcohol

The ester ($3.5\times10^{-3}$ moles) dissolved in ether (50 ml)+230 mg of $LiAlH_4$ are placed in a round-bottomed flask. The reaction is very exothermic with evolution of $H_2$. It is instantaneous. 5 ml of a 10N solution of $H_2SO_4$ are added to destroy the excess $LiAlH_4$. Extract with $CH_2Cl_2$ and wash the organic phase with water.

B-II. Perhydrogenated retinol with two carbon atoms:
I. Reaction:

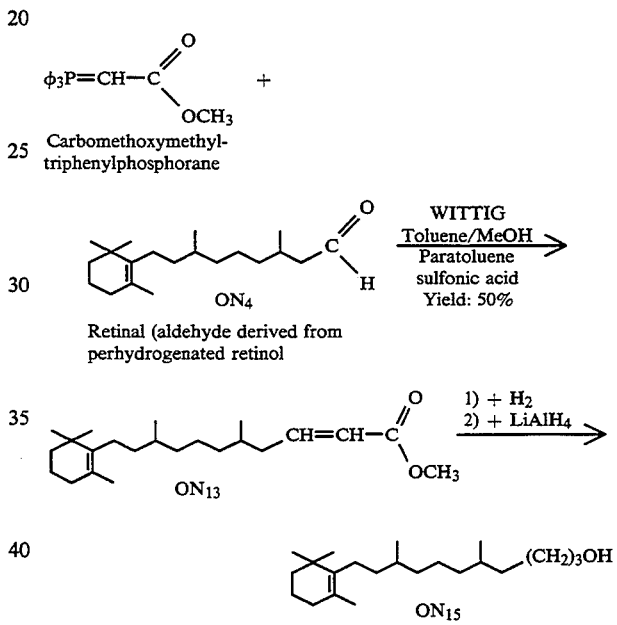

Retinal (aldehyde derived from perhydrogenated retinol

2. Procedure:
Preparation of retinal a. Anhydrous reaction. $CH_2Cl_2$ distilled from $CaH_2$ $5\times10^{-3}$ moles of pyridinium chromate+10 ml of $CH_2Cl_2$ are placed in a round-bottomed flask. A suspension is obtained to which $1.6\times10^{-3}$ moles of retinol dissolved in 5 ml of $CH_2Cl_2$ are added. The suspension then becomes black. The mixture is stirred under argon. Reaction time: 4 hours. Yield: 70%.

b. Several crystals of anhydrous paratoluene sulfonic acid+$1.7\times10^{-3}$ moles of (Carbomethoxymethylene)-triphenylphosphorane+distilled toluene (15 ml) are placed in a round-bottomed flask. The retinal dissolved in 5 ml of toluene is added followed by methanol (700 µl) to dissolve the ylid. The mixture is heated under argon at 95° C. Reaction time: 3 days. The reaction is stopped by the addition of a saturated solution of $NH_4Cl$. The ester obtained is reduced to the alcohol by reaction with $LiAlH_4$ as described above. The organic phase is extracted with ether. It is washed with water and the ether is evaporated.

B-III. Perhydrogenated retinol with three carbon atoms.

1. Reaction:

METHOD OF SYNTHESIS(2)

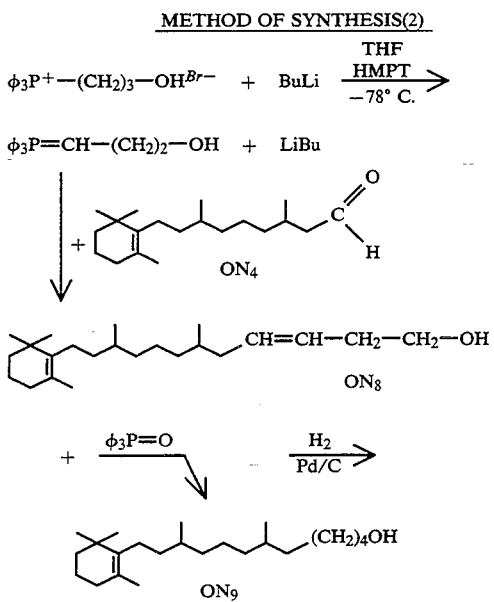

$\phi_3P^+-(CH_2)_3-OH^{Br-}$ + BuLi $\xrightarrow[-78°\,C.]{\text{THF}\atop\text{HMPT}}$ $\phi_3P=CH-(CH_2)_2-OH$ + LiBu ↓ + [perhydrogenated retinal aldehyde ON4]

[ON8: ring-CH=CH-CH2-CH2-OH structure]

+ $\phi_3P=O$ ↘ $\xrightarrow[\text{Pd/C}]{\text{H}_2}$

[ON9: ring-(CH2)4OH structure]

2. Procedure:

a. Anhydrous reaction. Anhydrous THF and HMPT. The phosphonium salt of anhydrous 3-bromopropanol ($4\times10^{-4}$ moles) is placed in a round-bottomed flask. THF (5 ml) and HMPT (0.5 ml) are added. The mixture is stirred and cooled to $-78°$ C. Three equivalents of BuLi are then added. The round-bottomed flask is then warmed to $-30°$ C. and the mixture is stirred for about one hour. When the salt has completely been dissolved, the solution is cooled again to $-78°$ C., the perhydrogenated retinal is added ($8\times10^{-4}$ moles) and the temperature is allowed to rise to room temperature overnight. Yield: 38%. The reaction is stopped by the addition of a saturated solution of $NH_4Cl$. The reaction mixture is extracted with ether and the extract is washed with water.

b. The product to be hydrogenated ($2\times10^{-4}$ moles) dissolved in 10 ml of neat MeOH is placed in a round-bottomed flask. Palladium on charcoal (10 mg) is added. Hydrogen is then passed through the mixture. The Pd/C is filtered off on celite and the methanol is evaporated.

Derivatives of vitamin A thus synthesized exhibit the following analytic properties:

| Product | MW | Rf | Elution solvent |
|---|---|---|---|
| n°1 | 330 | 0,42 | (TEA, Et2O, Hexane) (1, 10, 90) |
| N°2 | 340 | 0,547 | (TEA, Et2O, Hexane) (1, 10, 90) |
| n°3 | 298 | 0,573 | (TEA, Et2O, Hexane) (1, 60, 40) |
| n°4 | 288 | 0,28 | (TEA, Et2O, Hexane) (1, 60, 40) |
| n°5 | 296 | 0,8 | (TEA, Et2O, Hexane) (1, 50, 50) |

Derivatives of vitamin A

| Product | MW | Rf | Elution solvent |
|---|---|---|---|
| n°6 | 336 | 0,54 | (Hexane, ether) (50/50) |
| n°7 | 338 | 0,43 | (Hexane, ether) (50/50) |
| ON7: $C_8H_{16}O$ | 128 | 0,375 | (Hexane, ether) (60/40) |
| ON8: $C_{23}H_{42}O$ | 335 | 0,403 | (Hexane, ether) (60/40) |
| ON9: $C_{23}H_{44}O$ | 337 | 0,58 | (Hexane, ether) (60/40) |
| ON13: $C_{23}H_{40}O_2$ | 349 | 0,326 | (Hexane, ether) (90/10) |
| ON15: $C_{22}H_{44}O_2$ | 323 | 0,455 | (Hexane, ether) (60/40) |

| Product | MW | Rf | Elution solvent |
|---|---|---|---|
| $ON_{18}$: $C_{21}H_{37}N$ | 304 | 0,574 | (Hexane, ether) (80/20) |

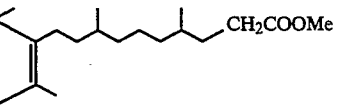

| | | | |
|---|---|---|---|
| $ON_{19}$: $C_{22}H_{40}O_2$ | 337 | 0,750 | (Hexane, ether) (80/20) |

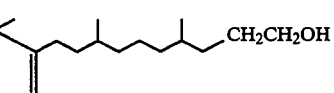

| | | | |
|---|---|---|---|
| $ON_{20}$: $C_{21}H_{40}O$ | 309 | 0,237 | (Hexane, ether) (80/20) |

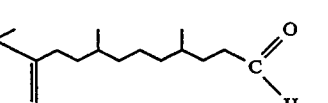

| | | | |
|---|---|---|---|
| $ON_{21}$: $C_{21}H_{38}O$ | 306,5 | 0,707 | (Hexane, ether) (80/20) |

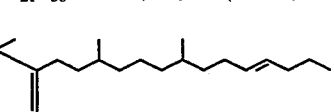

| | | | |
|---|---|---|---|
| $ON_{22}$: $C_{24}H_{44}O$ | 348,6 | 0,450 | (Hexane, ether) (60/40) |

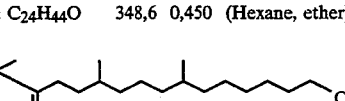

| | | | |
|---|---|---|---|
| $ON_{23}$: $C_{24}H_{46}O$ | 350,6 | 0,29 | (Hexane, ether) (80/20) |

TEA: triethylamine

The two hydrogenated derivatives of molecule No. 4 defined above, corresponding to the following formulae:

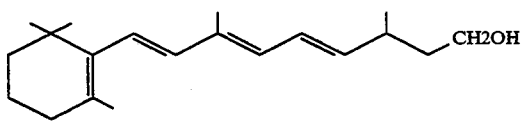

MW 290

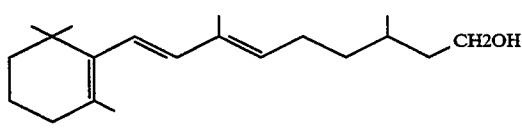

as well as the derivatives No. 6 and No. 7, ON7 to ON9, ON13, ON15, ON18 to ON20, are particularly active derivatives in the context of the present invention, in particular in the test described in example 1 (trophic effect on neurons in vitro) of Chapter II which follows.

2) Squalene derivatives

Reaction: Ozonolysis of squalene

A solution of 4 mmoles of squalene in 100 ml of $CH_2Cl_2$ and 1 ml of pyridine is treated with $O_3$ at $-70°$ C. for 2 hours. After addition of 1 ml of $(CH_3)_2S$, the reaction mixture is allowed to react for 1 hour at $-70°$ C., followed by 1 hour at 0° C., then it is extracted with $CHCl_3$. After evaporation of the solvent, the residue is chromatographed on $SiO_2$. Two products in particular are obtained with the desired biological activity: an alcohol with 27 carbon atoms and a diol with carbon atoms.

3) Hydrogenated derivative of geraniol (C20)

The derivative of formula $C_{15}H_{31}$-$CH_2OH$ was prepared by hydrogenation of geraniol.

Its analytical properties are the following:
PM=242,
Rf=0.454 in the elution solvent, $Et_2O$-Hexane (50/50).

4) Dimeric substances

A carotenoid containing two hydroxyl groups at the two ends of the molecule, decaprenyl astaxanthine is hydrogenated on Pd/C with ethanol as solvent.

5) Water-soluble derivatives of long chain alcohols: esters of monophosphoric acid.

a) monoester of monophosphoric acid

This reaction is applicable to linear alcohols, as well as to the derivatives and analogues of the terpenes and the cholesterol esters of the invention comprising a hydroxyl function, situated preferably at the end of a hydrocarbon chain. For the understanding of the account which follows, all of the derivatives cited above will be designated by the simplified expression $R_6$—OH which draws attention to the hydroxyl implicated in the phosphorylation reaction and in which $R_6$ represents the rest of these derivatives, namely more particularly a hydrocarbon chain of the type $R_1$—/A—$(X)_y$—$B/_p$ such as defined above.

A method of preparation is used which leads selectively to the monoester of the monophosphoric acid. This procedure makes use of bis(2,2,2-trichloroethyl) phosphochloridate as reagent and the Zn/Cu couple as deprotecting agent to generate the phosphate salt.

Preparation of the reagent

The reagent bis(2,2,2-trichloroethyl) phosphochloridate (BTEP) is prepared by the dropwise addition of trichloroethanol (44.8 g, i.e. 29 ml or 0.3 mole) during 15 minutes at $-50°$ C. Then the reaction is allowed to proceed at 0° C. for 2 hours under argon. The reaction mixture is heated at 55° C. overnight and distilled to give 16.7 g (0.046 mole, i.e. 15.3%) of bis(2,2,2-trichloroethyl) phosphochloridate B.p.=98° C. (0.15 mm Hg), $d_4^{15}$=1.75 g/ml.

Phosphorylation

The alcohol ($R_6$—OH) dissolved in 2 ml of THF (0.1 mmole) is cooled to $-78°$ C. 750 mg of molecular sieve 4A are added, followed by 43 μl (i.e. 0.21 mmole) of BTEP. The temperature is allowed to rise to room temperature; then the molecular sieve is removed by filtration. The filtrate is diluted with ethyl ether (10 ml). Then 5 ml of a 0.5 M solution of $NaHCO_3$ are added, followed by an ethereal solution of iodine (38 mg, 0.3 mmole in 5 ml of ethyl ether). The addition is made slowly and dropwise with vigorous stirring. After a reaction time of 20 minutes, an aqueous solution of $Na_2SO_3$ is added to destroy the excess iodine. The solution is washed with a saturated aqueous solution of NaCl and evaporated in a vacuum. Chromatography on $SiO_2$ with chloroformmethanol (50:1) as eluant gives the triester phosphate in a yield of 92%.

Removal of the trichlorethyl group.

65 mg of Zn/Cu and 50 μl (0.5 mmole) of acetylacetone are added to a solution of the phosphate triester previously obtained (0.05 mmole) dissolved in 1 ml of DMF. The solution is heated at 55° C. for 1 hour. The mixture is stirred in the presence of Chelex resin for 1 hour; then the resin is removed by filtration. The filtrate is evaporated to dryness. The residue is treated with formic acid (300 μl) and allowed to react for 24 hours, then evaporated to dryness and finally chromatographed on DEAE Sephadex (column: 0.9×12 cm) using a buffer pH 7.5 as eluant. The phosphate is then obtained in a yield of 75%.

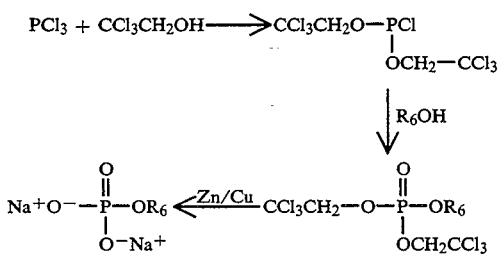

b) diester of the monophosphoric acid

This reaction is carried out by phosphorylation with o-phenylenephosphochloridate, followed by oxidative hydrolysis and makes it possible to obtain the diesters of the monophosphoric acid. This reaction is applicable to linear alcohols, as well as to the derivatives and analogues of the terpenes and the cholesterol esters of the invention, i.e. the derivatives of formula $R_6$—OH mentioned in the preceding paragraph. In this case, the $R_6$ group preferably represents a hydrocarbon chain of 8 to 28 carbon atoms, where appropriate substituted by one or more halogen atoms, in particular fluorine, or by one or more alkyl groups of 1 to 3 carbon atoms.

1st step: phosphorylation of the alcohols

An alcohol solution containing 1 mmole of a derivative of the invention (383 mg in the case of hexacosanol), represented by the expression $R_6$—OH ($R_6$ representing the remainder of the derivative of the invention, namely an alkyl chain of 26 carbon atoms in the case of hexacosanol) and 2,6-dimethylpyridine (110 mg, 1 mmole) is treated with a solution of 100 mg (0.5 mmole) of o-phenylene phosphochloridate in THF for 24 hours at 40° C. After addition of a saturated solution of $NaHCO_3$ (10 ml), extraction is performed with $CH_2Cl_2$ and chromatography on $SiO_2$ gives 330 mg of phosphate (85%).

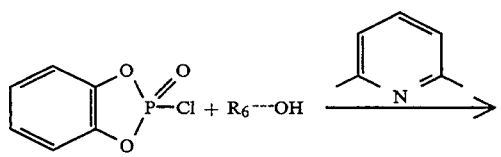

2nd step: hydrolysis followed by oxidation

The product previously obtained (330 mg) dissolved in 6 nil of THF is treated with a solution of 110 mg (1 mmole) of dimethylpyridine in 200 ml of water for 5 minutes, then extracted with chloroform ($CHCl_3$). The $CHCl_3$ extract is dissolved in THF (10 ml), then treated with 1 g of lead tetraacetate (Pb(OAc)$_4$); the mixture is adjusted to pH 10 with a 0.1N methanolic solution of potassium hydroxide (KOH). After evaporation of the solvent and washing with methanol (MeOH), the potassium salt is obtained in the form of a brown liquid which is purified by chromatography on $SiO_2$ using $CHCl_3$/MeOH/$H_2O$ 60:25:5 as eluant.

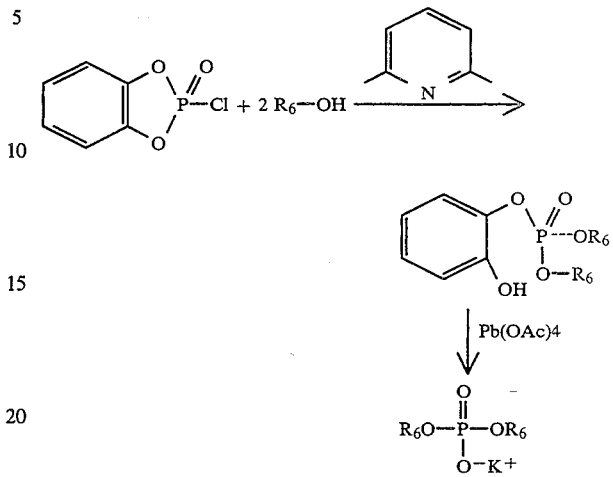

The ester of the monophosphoric acid of formula

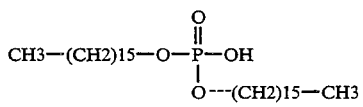

thus obtained possesses a MW of 547 and a Rf of 0.375 in the elution solvent: $CHCl_3$/methanol/$H_2O$ (65/25/4)

6) Substitution with fluorine atoms

It has been previously demonstrated that organofluorine derivatives may potentiate the effect of biological substances (Y. KOBAYASHI, I. KUMADOKI and T. TAGUCHI, Synthesis of biologically active fluorine compounds. Synth. Org. Chem., 38 (1980) 1119–1129). Using procedures already described for the incorporation of fluorine atoms (KOBAYASHI et al., above; J. T. WELCH, Advances in the preparation of biologically active organofluorine compounds. Tetrahedron, 43 (1987) 3123–3197; Biomedical aspects of fluorine compounds, R. FILLER and Y. KOBAYASHI eds, KODANSHA, Tokyo, (1982)), it was found that the substitution of fatty alcohols with 26±6 carbon atoms with 1 to 5 fluorine atoms improves the bioavailability of the molecules.

Fluorination takes place by an electrophilic mechanism.

The substitution may be performed on a saturated C—H bond (D. BARTON and D. OLLIS, in Comprehensive Organic Chemistry, J. F. STODDART, ed. Pergamon Press (1979) pp. 504–507). Electrophilic attack occurs directly at the C—H bond.

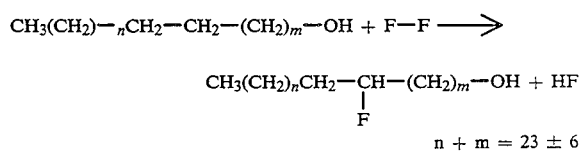

n + m = 23 ± 6

Substitution may also take place by saturating one or more unsaturated systems by compounds containing one or more fluorine atoms.

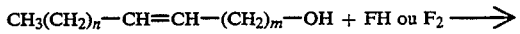

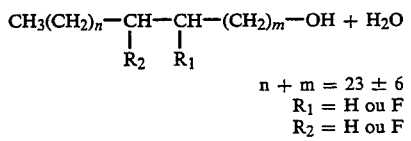

The fluorinated compounds containing 1 to 5 fluorine atoms improve the bioavailability of the molecule and increase their biological efficacy.

Difluorinated derivatives are particularly interesting the point of view of their biological activity (T. MORIKAWA et al., Studies on Organic Fluorine Compounds. Synthesis of 2,2 difluoro arachidonic acid. Chem. Pharm. Bull., 37 (3) 813–815 (1989)). They are obtained in the following manner:

Detailed reaction:

A solution of the $C_{24}$ aldehyde (32 mmole) and ethyl bromodifluoroacetate (28.04 mmole) in THF (33 ml) is added dropwise to a mixture of Zn (33.35 atomic mass) and THF (30 ml). The mixture is heated under reflux for 3 hours with stirring. After the addition of ether and aqueous $NH_4Cl$, the precipitate is removed by filtration and the filtrate is extracted with ether, the extract is washed with a NaCl solution, then chromatographed on $SiO_2$. The compound is then treated with a 1N solution of HCl and hydrogenated in the presence of $PtO_2$. The ethyl ester of the $C_{26}$ acid is obtained in a yield of 57%. This ester is then reduced by means of $LiAlH_4$ in ethyl ether by heating under reflux.

with blood of the affected nervous tissue and limit the proliferation of fibroblasts or astroblasts at the site of the lesion.

These properties are demonstrated with the aid of neurons maintained in primary culture under different conditions or in vivo with the aid of various models of experimental lesion in animals (GAGE et al., Brain Res., 268: 27-37 (1983); WILLIAM et al., Proc. Natl. Sci. 83: 9231-9235 (1986)). The doses used are of the order of 0.01 mg/kg, more particularly 0.1 mg/kg to 5 mg/kg. On account of the improved bioavailability of the molecules which we describe and their greater efficacy at the level of the cell membrane, we improve the effects previously observed with n-hexacosanol at lower doses (BORG et al., Neurosci. Lett., 213: 406-410 (1987)).

Furthermore, the derivatives of the invention also promote the regeneration of peripheral nerves. Following a traumatism of the peripheral nerve, there may be loss of nervous continuity, followed by wallerian degeneration. The use of the derivatives of the present invention makes it possible in this case to reduce the size of the lesions and to facilitate the restoration of nervous continuity. This result is obtained owing to the neurotrophic and regenerative properties of these derivatives.

EXAMPLE 1

SURVIVAL AND REGENERATION OF CEREBRAL NEURONS IN THE PRESENCE OF DERIVATIVES AND ANALOGUES OF THE LONG CHAIN FATTY ALCOHOLS OF THE INVENTION.

The use of cerebral neurons maintained in primary

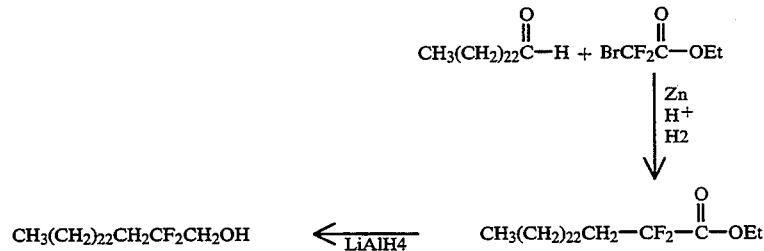

MW = 316 to 502.

II BIOLOGICAL ASSAYS IN VITRO and IN VIVO

1) Nerve regeneration

The derivatives and analogues of the long chain fatty alcohols of the invention play a role in the control of the plasticity of nerve tissue during development and in the adult. They increase neuronal survival during phases of development which see the establishment of new neuronal connections and also in the adult during the processes of learning and memory. As we describe in example 1 which follows, the derivatives of the invention promote neuronal differentiation as well as the survival of neurons. This property gives them the capacity to increase the survival of neurons injured as the consequence of a traumatism. The derivatives and analogues of the long chain fatty alcohols of the invention promote the survival and the regeneration of neurons subsequent to a traumatism of the cerebrum or spinal cord. These molecules are capable of limiting the extension of the lesions, reducing wallerian degeneration and promote axonal regeneration. In particular, the molecules described diminish post-ischemic necrosis, reduce the edema surrounding the lesion, increase the perfusion culture makes it possible to demonstrate the activity of neurotrophic factors (G. BARBIN, I. SELAK, M. MANTHORPE and S. VARON; Neuroscience, 12 (1984) 33–43). Neuronal cultures are prepared from the cerebrum of 13 to 18 days old rat embryos. The cells are inoculated at low density (10,000 to 100,000 cells per ml); they grow in Petri dishes coated with a polylysine support in the presence of a culture medium which is prepared from the Eagle-Dulbecco medium (R. DULBECCO and G. FREEMAN, Virology, 8, (1959) 396) to which supplements of insulin, transferrin, progesterone, selenium and putrescine are added (BORG et al., Develop Brain Res. 18: 37–49 (1985)). The derivatives tested are added at the beginning of culture at doses varying from $10^{-8}$ to $10^5 M$.

The development of the culture is followed with the aid of a phase contrast microscope. Staining with trypan blue enables the number of neurons which put out extensions to be measured. It is observed that in the control cultures the number of live neurons and neurons with extensions diminishes after a certain period of culture. Conversely, in the cultures treated with the derivatives of the invention, the number of these neurons remains constant with time and the length of the extensions is much greater than in the controls. A large number of ramifications projecting from these extensions and the existence of numerous cell contacts are also noted. In vivo, these observations correspond to the establishment of new neuronal circuits and to the formation of intercellular or synaptic junctions.

The increase in the survival of neurons placed under critical conditions and the improvement of their morphological maturation is also expressed by enhanced maturation from the biochemical standpoint.

It is possible to measure the presence of certain specific proteins of these neurons, such as the proteins of the neurofilaments, the neurospecific enolase or glutaminase by immunocytochemical methods or enzymatic methods. After fixation, the cells are incubated with a specific antibody to a neurofilament or to the enolase after different times of culture. The presence of these proteins is revealed by a method employing peroxidase or with fluorescent antibodies. These proteins make their appearance earlier and are more dense in cultures containing the derivatives of the invention.

It is also possible to measure the enzymatic activity of the enolase or the glutaminase which are good markers of neuronal maturation (BORG et al., Neurosci. Lett., 213: 406–410 (1987)). The enzymatic activity relative to the amount of protein makes it possible to compare the neurotrophic effect of the various derivatives of the invention. This quantitative measure shows that the effect is observed early and continuously; it also makes it possible to make correlations between the dose used and the response observed. In all cases, the neurons treated with the derivatives and analogues of the long chain fatty alcohols of the invention induce an enhanced activity of the markers of maturation compared with the controls.

The derivatives of the invention have a greater effect than the other neurotrophic factors already known on account of their improved bioavailability and a higher efficacy at the cellular level. These results show that the derivatives and analogues of the long chain fatty alcohols promote the survival of cerebral neurons and increase their degree of maturation.

Examples of the increase of neuronal survival brought about with the aid of the derivatives ON13, ON9 and ON8 are shown in FIG. 1.

2) Neuroprotection

Another interesting application of the derivatives of the invention is associated with their property of protecting the neurons with lesions due to the presence of neurotoxic substances such as glutamate, ibotenic acid, AF-64, scopolamine or N-methyl-D-aspartate. The excitatory neurotransmitter glutamate and the excitotoxins in general produce neurotoxic effects which are related to their depolarising action at their receptors. Some analogues of glutamate, such as ibotenic acid or quisqualate have more potent excitatory effects and also produce neurotoxic effects. The neuroprotective properties of the derivatives of the invention have been demonstrated following an injection of a neurotoxic substance, ibotenic acid, into the basal nucleus of the rat (Example 2). This injection causes behavioral disorders, with a perturbation of the capacities of memory and of learning and locomotor hyperactivity. From the biochemical point of view this lesion leads to a diminution of the production of acetylcholine and of the activity of choline acetyl transferase in the ipsilateral neocortex, as well as morphological lesions in this area of the cerebrum. It should be recalled that this type of lesion is found in patients suffering from Alzheimer's disease (WENK et al., Brain Res., 293: 184–186 (1984)). These lesions are appreciably reduced in animals which have received intraperitoneal injections of the derivatives of the invention at a dose of 1 mg/kg/day.

The derivatives and analogues of the long chain fatty alcohols of the invention may thus be used in the treatment of neurodegenerative diseases such as Huntington's chorea, Alzheimer's or Parkinson's disease. They also make it possible to improve the treatment of epilepsy and other behavioral disorders associated with the limbic system. Furthermore, they are capable of inducing protection of the neurons against neurotoxins, certain ions and oxidising radicals. For all of these uses, the therapeutic doses are of the order of 0.1 mg/kg/day to 10 mg/kg/day. They are given by repeated administration by the parenteral or oral route.

EXAMPLE 2

PROTECTION AGAINST LESIONS DUE TO NEUROTOXIC SUBSTANCES

The excitotoxic properties of an amino acid, ibotenic acid, are used to study the survival of the cholinergic neurons of the basal nucleus, according to a method previously described (WENK et al., Brain Res., 293: 184–186 (1984)). After Long-Evans male rats have been anaesthetized, they are placed in a stereotaxic apparatus; then, 25 nmoles of ibotenic acid are injected into the left side of the basal nucleus.

One group of rats is treated with a derivative of a long chain fatty alcohol by being given one injection per day (1 mg/kg) by the intraperitoneal route beginning two days before the injection of ibotenic acid.

It is possible to use several types of cognitive and behavioral tests during the experiment, in particular the radial labyrinth with 8 branches, the learning labyrinth of Hebb-Williams, or the swimming pool test (ALFORD et al., Exp. Brain Res., 69 (1988) 545–558)). The animals treated with ibotenic acid show a deficiency of the capacities of learning and memorization. A deficit is also observed in spatial localization, similar to that observed in Alzheimer's disease. In the case of the treated animals the deficiencies are markedly less and the capacities of learning and memorization are maintained.

On completion of the behavioral tests, the animals are sacrificed in order to carry out a histological analysis of the area of the basal nucleus. A loss of substance induced by ibotenic acid is observed which is markedly more limited in the case of the treated animals. The lesion which in the case of the controls extends in all directions from the site of injection towards the globus pallidus is less extensive after treatment and corresponds to the injection of a smaller amount of neurotoxin. Biochemical assays are also carried out on the neocortex and the hippocampus. The activity of choline acetyl transferase is diminished in the frontal, temporal and pariental cortex as well as in the amygdala two weeks after injection of ibotenic acid. Treatment with the derivatives of the invention leads to an appreciable reduction of this deficit in these regions and progressive recovery of the choline acetyl transferase activity during the weeks which follow the injection.

The derivatives of the invention make it possible to protect certain cerebral neurons against lesions induced by excitotoxic amino acids and against the functional consequences of these lesions.

3) Repair of lesions

Cellular regeneration also occurs during the repair of vascular or cutaneous lesions. Thus the vascular endothelium is composed of a monolayer of cells which line the internal face of the cardiovascular system. This monolayer represents a surface of several hundreds of $m^2$ and plays a major role in vascular integrity. The endothelial cells produce many substances which participate in coagulation, fibrinolysis and inflammatory phenomena. The impairment of these functions may lead to an increase in vascular permeability and to an accumulation of proteins and lipoproteins in the interstitial tissue or to the adhesion of platelets to the sub-endothelium accompanied by the secretion of "platelet-derived growth factors" (PDGF), and finally to the migration and proliferation of smooth muscular cells. An impairment of the vascular endothelium is thus an important first step in the phenomena of thrombosis and atherosclerosis (Cazenave et al. Inter Angio 3:27–32 (1984)). Following a lesion to the vascular endothelium, several phenomena appear in the in vivo repair process: first of all, the migration and replication of endothelial cells, platelet adhesion to the exposed sub-endothelium and finally the proliferation of smooth muscle cells which leads to the formation of plaques and to atherosclerosis. Derivatives making it possible to protect the vascular wall or to inhibit platelet adhesion may thus prevent the formation of plaques and atherosclerosis.

One of the applications of the invention consists of using the derivatives described above to promote the repair of cutaneous or vascular lesions. The lesions to the endothelial cells lead to the formation of deposits of proteins or lipoproteins in the interstitial tissue as well as to the proliferation of smooth muscle cells. These phenomena constitute the first stage in the development of thrombosis and atherosclerosis (R. Ross. Atherosclerosis 1:293–311 (1981)). The derivatives of the invention enhance the differentiation of the cells of the dermis, epidermis and of the vascular endothelial cells. As we show in Example 3, these derivatives accelerate the repair of a mechanical lesion to vascular endothelial cells. This property is demonstrated with the aid of an in vitro model of a mechanical lesion to human endothelial cells in culture. The cultures are obtained from human umbilical veins and are maintained in a RPMI medium plus HEPES plus 30% human serum; the lesion is made 3 days after confluence by the application of a cellulose disc to a confluent layer of endothelial cells (C. Klein-Soyer et al., Thrombosis Haemostasis 56:232–235 (1986)). The rate of regeneration depends on the size of the initial lesion and the concentration of serum. Furthermore, the addition to the culture medium of the derivatives of the invention significantly increases the surface of the initial lesion covered by the endothelium which regenerates. The doses used are of the order of 0.01 to 100 $\mu$M, more particularly 0.1 to 10 $\mu$M. The corresponding doses for use in vivo are of the order of 0.01 mg/kg to 100 mg/kg, more particularly 0.1 to 10 mg/kg.

The use of the derivatives of the present invention makes it possible to accelerate the repair of cutaneous or vascular lesions and to retard the degeneration of the cells of the skin associated in particular with ageing as a result of exposure to U.V. radiation and aggressive chemical agents. This property is demonstrated in vitro with the aid of cultures of keratinocytes. The long chain fatty alcohols of the invention increase the survival of these cells placed under unfavourable conditions or in the presence of factors which lead to degeneration of these cells. They accelerate their differentiation ad well as the repair of tissue lesions. The doses used are similar to those described for the vascular lesions.

EXAMPLE 3

REPAIR OF LESIONS TO THE VASCULAR ENDOTHELIUM BY LONG CHAIN FATTY ALCOHOLS.

Models of a mechanical lesion to a layer of endothelial cells in vitro make it possible to study the processes of repair of this type of lesions (C. Klein-Soyer et al. mentioned above). The endothelial cells are isolated from human umbilical veins. They are incubated with 0.1% collagenase for 15 min at 37° C. and the effluent is recovered in tubes containing culture medium (RPMI, HEPES, glutamine and 5 to 30% of human serum). After centrifugation, the pellet is inoculated onto Petri dishes pretreated with fibronectin which serves as support.

The lesion is made on confluent cultures by application of a calibrated disc of cellulose polyacetate. This procedure selectively detaches the endothelial cells which were present in the area to which the disc was applied. Then the long chain fatty alcohols are added to the culture medium at doses varying from 0.01 $\mu$M to 100 $\mu$M, and preferably from 0.1 to 10 $\mu$M.

After the lesion has been made, the dishes are removed every 24 h in order to measure the size of the lesion. Adhesive grids divided into squares of 0.5 $mm^2$ are used which are applied to the bottom of the dish coincidentally with the lesion. The surface of the lesion is measured by counting the squares with an inverted microscope. The rate of regeneration is linear for 48 h, then it slows down when the lesion is only 75 to 80% of the initial lesion. The presence of the derivatives of the invention increases the rate of regeneration so that it requires shorter time and even occurs in the absence of human serum from the culture medium. Furthermore, in the absence of serum the beginning of the degeneration of the endothelial cells is observed, and this is not the case when long chain fatty alcohols are present.

In vivo a lesion of the vascular endothelium may lead to the adhesion of platelets, the proliferation of smooth muscle cells and the development of thrombosis or plaques of atherosclerosis. With the aid of the model of mechanical lesion, it is observed that the long chain fatty alcohols of the invention protect the vascular wall and improve the capacities of regeneration of the latter. The physicochemical properties of these derivatives and their good bioavailability make them particularly useful therapeutic tools in the treatment and prevention of thrombosis and atherosclerosis.

4) Cytoprotection

Certain cellular lesions are associated with the presence of toxic substances or are the consequence of an ischemia, as in nervous tissue. These phenomena are particularly significant in the liver, cardiac muscle and the kidney. Some molecules (xenobiotic) may impair the functions of hepatic cells either directly or after conversion of these molecules into a more toxic form. The cellular lesion may start either by the formation of a stable complex with a protein or other intra-cellular compound, or by the formation of a very reactive chemical entity or by inducing physico-chemical changes in the cells or in its environment (Bridges et al., Ann N.Y. Acad. Sci. 407: 42–63 (1983)). The cellular lesion may be limited or prevented by certain systems of defense, such as the enzymes implicated in the metabolism of medicines, of binding proteins or antioxidants. It is possible to use isolated hepatocytes as an experimental model to study the toxicity of certain molecules. The cytotoxicity is measured by the release of cytosolic enzymes, the secretion of albumin, morphological changes observed in the optical microscope and by the determination of cellular viability. The cellular lesion is affected by its environment, in particular the partial pressure of oxygen or the presence of extra-cellular calcium. The toxicity of certain drugs is potentiated by the depletion of glutathione. The use of isolated hepatocytes maintained in culture makes it possible to study the hepatic cytotoxicity and also to detect compounds which protect against cytotoxic substances. It is possible to study in particular the levels of the cytochromes P450 and of the enzymes involved in the metabolism of medicines, such as glucuronyltransferase and sulfotransferase.

Similarly, it is possible to study the cytotoxicity of certain molecules on cells of the glomerulis or the renal tubule with the aid of isolated tubular, epithelial or mesangial cells. The cytotoxicity is measured by morphological changes or by the expression of biochemical functions specific to these cells (secretion of an inhibitor of the plasminogen activator, PGE2, interleukin 1) (J. D. Sraer et al., FEBS Lett. 104: 420–424 (1979)).

In particular, the long chain fatty alcohols of the invention increase the synthesis and secretion of activators of plasminogen by 70 to 100% compared with the control in epithelial and mesangial cells of the human kidney. The maximal effect is obtained at doses varying from $10^{-5}$ to $10^{-7}$M. This result leads to the expectation of a pharmacological action in coagulation phenomena and in the formation of extra-cellular matrices. The molecules of the invention may also prevent the propagation of metastases derived from cancerous tumors and in doing so to combat the action of certain proteins.

The increase in the synthesis of tPA (tissue plasminogen activator) by the mesangial cells in the presence of n-hexacosanol is shown in FIG. 2.

As far as cardiac muscle is concerned, the cellular lesions are usually the consequence of an ischemia. Isolated cardiac muscle cells make it possible in particular to follow the development of the lesions from the point of view of electrophysiological changes (P. Athias et al. In Vitro 22:44 (1986)).

The long chain fatty alcohol derivatives of the invention play a role in the protection against chemical lesions or both associated with an ischemia which occur in hepatic, renal or cardiac muscle cells.

The presence of toxic substances or an ischemia causes cellular degeneration which is expressed by the release of cytosolic enzymes (LDH), morphological changes, a loss of cell viability. It is possible to use cells in culture to demonstrate this toxicity and possible protective agents. As we demonstrate in Example 4, the derivatives of the invention increase the survival and support the differentiation of hepatocytes maintained in culture. The cultures are obtained by disruption of adult rat liver and are maintained in a Ham/F12 medium supplemented with albumin, insulin, hydrocortisone and 10% of fetal calf serum. The survival of the hepatocytes in vitro is limited, they have a tendency to lose some characters of differentiation and to degenerate in the presence of toxic substances. It is particularly so in the case of galactosamine, paracetamol, pentobarbital (Paine and Hockin. Toxicology 25:41 (1982) or cyclophosphamide (ACOSTA and MITCHEL. Biochem. Pharm. 30:3225 (1981)).

The addition of long chain fatty alcohols to the culture medium improves the survival of the hepatocytes in vitro since this can be measured in viability tests, by the level of glutathione and the cytochrome P450 activity as well as the secretion of albumin (Le Rumeur et al. Exp. Cell Res. 147:247–254 (1983)). These derivatives of the invention also diminish the toxicity of pentobarbital or cyclophosphamide, as can be observed from morphological changes, the diffusion of cytosolic enzymes and the activity of detoxification enzymes, such as the cytochromes P450, the monooxygenases and the conjugation enzymes. The doses used are of the order of 0.01 to 100 $\mu$M, more particularly 0.1 to 10 $\mu$M. The corresponding doses for the use in vivo are of the order of 0.01 mg/kg to 100 mg/kg, and more particularly 0.1 to 10 mg/kg.

The use of the derivatives of the present invention makes it possible to protect hepatic, renal or cardiac muscle cells against degeneration due to toxic substances or to an ischemia. The protective effect for cells of the renal glomerulis is also demonstrated with the aid of mesangial, epithelial or tubular cells in vitro. It is possible to measure the effect on cellular degeneration by morphological changes and by the expression of specific biochemical functions, such as the secretion of an inhibitor of the plasminogen activator, PGE2, interleukin 1 (J. D. Sraer et al., mentioned above). It is possible to measure the effect on the degeneration of cardiac muscle cells, in particular after an ischemia, by morphological changes, the diffusion of cytosolic enzymes (LDH) or modifications of the excitatory properties of membranes (P. Athias et al., mentioned above). The doses used are similar to those described for the cytoprotective effect for hepatocytes.

The derivatives of the present invention make it possible to protect intestinal and gastric cells against toxic substances, such as an excess of gastric acidity. The molecules of the invention make the parietal and epithelial cells of the stomach more resistant to an excess of gastric acidity; they reduce the secretion of H$^+$ ions and increase the secretion of mucus. This effect makes it possible to protect this organ against the consequences of stress, to regulate intestinal motoricity in a situation of stress and prevent the formation of a gastric or intestinal ulcer. The derivatives of the invention also increase the trophicity of the intestinal villi, of the epithelial cells of the stomach and of the Langerhans islets of the pancreas. They make the intestinal mucosa more resistant in situation of malnutrition and limit the functional consequences associated with a pancreatitis, in particular on the secretion of insulin. The derivatives of the invention are added advantageously to preparations intended for parenteral alimentation or to substitutes for mother's milk. They promote the differentiation and maturation of the tissues of the digestive tract during development or following a chemical, mechanical or surgical traumatism.

EXAMPLE 4

PROTECTION OF HEPATIC CELLS AGAINST DEGENERATION INDUCED BY TOXIC SUBSTANCES.

The maintenance in culture of isolated hepatocytes makes it possible to study their metabolism and their sensitivity to certain toxic substances. The hepatocytes are isolated from adult rat liver by perfusion with collagenase, filtration and centrifugation in the L15 medium. The hepatocytes are purified by elutriation in an elutriation chamber at a flow rate of 10 to 40 ml/min which is centrifuged at 840 revolutions per min (E. Le Rumeur et al. mentioned above). A pure fraction containing diploid hepatocytes is obtained at a flow rate of 15 ml/min. They are inoculated on Petri dishes covered with a layer of fibronectin in the Ham/F12 medium containing bovine albumin, insulin, 10% fetal calf serum and hydrocortisone. Long chain fatty alcohols are added to some of the dishes at doses varying from 0.01 $\mu M$ to 10 $\mu M$, and preferably from 0.1 to 10 $\mu M$.

It is possible to measure the differentiation of the hepatocytes by measuring the production of albumin by immunonephelometry and protein synthesis by the incorporation of labelled leucine. It is also possible to measure the level of glutathione and the activity of enzymes implicated in the metabolism of medicines such as cytochrome P450, the glucuronyltransferases and the sulfotransferases. The cells have a tendency to degenerate when they are kept in culture and, in particular lose their cytochrome P450 activity and the conjugation enzymes. On the other hand, the cultures treated with the molecules which we have described have a higher level of survival and conserve their enzymatic activities. These results show the cytotrophic effect of these molecules.

The addition of certain drugs such as galactosamine, paracetamol, pentobarbital or cyclophosphamide during 24 h at doses from 0.1 to 1 $\mu M$ leads to the degeneration of hepatocytes which is reflected in biochemical and morphological changes. The cells release cytosolic enzymes into the culture medium (such as LDH), cell viability is diminished as is the capacity of albumin secretion and the level of glutathione. Degeneration is attenuated appreciably in the cultures treated with long chain fatty alcohols of the invention, with improvement in survival and maintenance of the characters of differentiation of the hepatocytes.

These results show the value of the derivatives of the invention in the treatment of toxicity induced by certain drugs and as protectors against the degeneration of hepatic cells.

5) Immune defenses

A defect in the expression of the differentiated functions of certain cells may result in a deficit in the immune defenses of the organism. These latter depend in particular on the macrophages which secrete cytokines which participate in the regulation of immunity. Interleukin 1 is secreted by the macrophages; it promotes the proliferation and differentiation of the lymphocytes by increasing the appearance of receptors for IL2 (Hogan and Vogel. J. Immunol. Immunopharmacol. 8:6–15 (1988)). It also promotes the differentiation of the B lymphocytes and the secretion of antibodies. The macrophages also secrete a molecule called "Tumor Necrosis Factor" (TNF) which leads to the lysis of tumors, and another called "Colony Stimulating Factor" (CSF) which may promote the production of interferon in the medulla. This CSF is itself an agent of differentiation for the precursors of the macrophages; it increases the response of the macrophages to certain differentiation agents such as phorbol ester. Finally, the macrophages produce and $\beta$ interferon in response to certain stimuli. Interferon enhances the phagocytic functions of the macrophages and hence their tumoricidal role.

The immune defenses also depend on the lymphocytes. These latter may differentiate into monocytes or granulocytes in response to certain agents. Thus, a phorbol diester promotes the differentiation of lymphocytes into monocytes (Royera et al., Proc. Natl. Acad. Sci. 76:2779 (1979)) and the retinoids promote the differentiation of lymphocytes into granulocytes (Breitman et al., Proc. Natl. Acad. Sci. 77:2939 (1980)).

Another interesting application of the present invention consists of promoting the differentiation of the cells which participate in the immune defenses of the organism, such as the macrophages, the monocytes and the lymphocytes. It is possible to measure the degree of differentiation of these cells by their capacity to secrete certain cytokines, such as IL1 (interleukin-1), CSF or interferon as well as by their response to immune signals (Waren and Ralph., J. Immunol., 137:2281 (1986)). The addition of long chain fatty alcohols of the invention has a cytotrophic effect on these cells and increases the production of CSA (Colony Stimulating Activity) by the monocytes in response to PMA, increases the production of interferon and interleukin-1 by the macrophages, increases their phagocytic functions as well as their receptiveness to immune signals. The derivatives of the invention also promote the proliferation and differentiation of the peritoneal and cerebral macrophages; they thus enhance their cytotoxic and phagocytic capacities which increases the defenses of the organism during the course of a bacterial or viral infection (AIDS in particular). The capacity to act at the level of the CNS makes them particularly useful in the case of cerebral attack by viruses (HIV in particular). These substances also enhance the LAK (Lymphokine activated killer) activity of the T lymphocytes as well as the cytotoxic activity of some of the T lymphocytes (they stimulate the secretion of IL-2 in the lymphocyte). If blood monocytes are incubated in the presence of the derivatives of the invention, an improvement in their survival is observed after 5 days, a more advanced differentiation in terms of quality and number of cells differentiated (appearance of a specific surface antigen, secretion of certain lymphokines). An increased production of IL1 promotes the activation of the B and T lymphocytes, increases the number of receptors for IL2, induces a granulocytosis. The doses used in vitro are of the order of 0.01 to 10 $\mu M$, and more particularly 0.1 to 5 $\mu M$. The corresponding doses for use in vivo are of the order of 0.01 mg/kg to 10 mg/kg, and more particularly 0.1 to 5 mg/kg.

The trophic action of the derivatives of the invention on the lymphocytes and the macrophages enables them to be used to promote the immune defenses of the organism, in particular in the case of a deficit in the immune system (AIDS, auto-immune diseases).

6) Anti-inflammatory and anti-allergic effect

Histamine plays an essential role in the pathology of inflammation; it is also one of the mediators of allergic or anaphylactic phenomena. It is released by the mastocytes or basophilic leukocytes. The release of histamine by the mastocytes might also play a role in the control of the cutaneous microcirculation. Apart from this non-immunological phenomenon, it is recognized that the stimulation of the basophils and mastocytes by an antigen and of the IgE is a basic mechanism in acute allergic diseases such as anaphylactic shock, asthma, allergic rhinitis and certain diseases of the skin such as urticaria and atopical dermatitis (J. C. Foreman, Ann. Rev. Pharmacol. Toxicol. 21: 63–81 (1981)).

The IgE antibodies are secreted by B lymphocytes in response to the binding of an antigen. This secretion is controlled by other lymphocytes, the suppressor T lymphocytes and the helper T lymphocytes. The IgE is then bound to the mastocytes and to the basophils and leads to the release of histamine together with other mediators of inflammation. The crosslinking of the IgE is necessary in order to produce this response and the amount of histamine released is related to the number of crosslinked IgE molecules. The release of histamine also requires the presence of extracellular calcium as well as the activation of the metabolism of the inositol phosphates and the intervention of cyclic nucleotides. A certain number of substances which interact either with the calcium flux or with the metabolism of the inositol phosphates or with that of the cyclic nucleotides, such as theophylline, modify the response of the mastocytes and basophils to the binding of the IgE.

Finally, the physiological response to the secretion of histamine and other mediators of inflammation (leukotrienes, prostaglandins) is mediated by the binding of these molecules to their target, in particular the smooth muscles. Let us cite as an example bronchial vasoconstriction, subsequent to the release of histamine and which occurs in asthma.

The long chain fatty alcohol derivatives of the invention exhibit a cytotrophic effect on cells which participate in the inflammatory and allergic phenomena of the organism, such as the mastocytes and the basophilic leukocytes. Inflammatory and allergic phenomena are triggered by the binding of an antigen and the IgE's to these cells, and this leads to the release of histamine. It is possible to measure the histamine released by mastocytes derived from the peritoneal fluid by incubating them for 30 min at 37° C. in a defined medium. The amount of histamine secreted increases with the concentration of calcium in this medium or in the presence of the ionophore A23187; histamine is also secreted following the binding of IgE to the cell membrane and to the crosslinking of these molecules (J. C. Foreman mentioned above). If derivatives of the invention are added to the incubation medium, the amount of histamine released is significantly diminished. This suggests that they act on the calcium fluxes or on the movement of the receptors for IgE in the membrane or also on secondary mechanisms implicated in the process of exocytosis (metabolism of the inositol phosphates, cyclic nucleotides), resulting in a reduction in the secretion of histamine and hence an anti-inflammatory effect. This effect is obtained in vitro with amount of long chain fatty alcohols of the order of 0.01 to 100 $\mu$M, and more particularly 0.1 to 10 $\mu$M. The corresponding doses for in vivo use are of the order of 0.01 mg/kg to 100 mg/kg, and more particularly 0.1 to 10 mg/kg.

The derivatives of the invention thus make it possible to attenuate the inflammatory and acute allergic processes resulting from the secretion of IgE and the binding of an antigen to the mastocytes and the basophils, as may be observed in asthma, allergic rhinitis, anaphylactic shock or urticaria.

The derivatives of the invention protect cartilaginous and bone tissue from the consequences of an acute or chronic inflammation, such as may be observed in any inflammation of the articulations or the bones. In particular they slow down the destruction of bone and the development of arthrosis. This effect is obtained as a result of a trophic effect of the long chain fatty alcohols on the chondrocytes and the osteoblasts, as well as a stimulatory action on the differentiation of these cells during development or following a traumatism.

7) Anti-tumoral effect

Each cell may be identified by morphological, biochemical and immunological criteria representative of a given state which may change under the influence of an activation. The activation phenomena appear rapidly after stimulation: they are variations in calcium mobilization, in the DNA, RNA or protein content; they result in the expression of membrane antigens or in the induction of enzymatic activities. In the case in which the stimulation leads to the acquisition of specific characters, antigenic or functional, corresponding to a cell state more mature than the initial state, the activating signal is a signal for differentiation. These effects are observed with diverse cell types, such as central neurons with hexacosanol (Borg et al., FEBS Lett. 213: 406–410 (1987)), but also human promyelocytes which differentiate into monocytes in the presence of phorbol diester (G. Rovera et al., Proc. Natl. Acad. Sci. 76: 2779–2783 (1979)) or into granulocytes under the influence of retinoids (T. R. Breitman et al., Proc. Natl. Acad. Sci. 77: 2936–2940 (1980)).

In the case of the promyelocytic cells, the direction in which differentiation is oriented may be defined using phenotypic markers, such as the expression of membrane antigens M02, specific for monocytes, or M01, characteristic of the differentiation into granulocytes or monocytes. Certain inducers have the capacity to differentiate cancerous or precancerous cells into differentiated cells. Other molecules such as the TNF also have an anti-cancerous activity. This TNF is secreted by the macrophages; it can cause lysis of tumors. The cytotoxic activity is exerted by monocytes activated by the TNF (E. A. Carswell et al., Proc. Natl. Acad. Sci. 25: 3666 (1975)). This toxicity is selective for tumor cells and it may be supposed that this substance plays an essential role in the defense of the organism against neoplasia. Any molecule which would promote the differentiation of the macrophages or the monocytes and their production of TNF might thus enhance the defensive capacities of the organism.

Another application of the invention consists of promoting the differentiation of the cells which participate in the defense of the organism against tumor processes, such as the macrophages, the lymphocytes and the monocytes. When they attain their differentiated state, these cells show a phagocytic activity and the release of tumoricidal molecules, such as the TNF. The promyelocytic cells may differentiate into monocytes or granulocytes under the influence of certain inducers such as the phorbol esters or the retinoids. It is possible to measure the differentiation of these cells with the aid of HL60 leukemic promyelocytic cells maintained in culture in a RPMI medium containing 20% of fetal calf serum. The cells are placed in culture at a concentration of $3 \times 10^5$ cells per ml and subcultured twice per week (N. Mendelsohn et al., Cancer Res. 40: 1469–1474 (1989)).

The derivatives of the invention are added to the medium at the time the cells are placed in culture and the degree of differentiation is measured 5 days after the start of the treatment by the changes in morphology and by their capacity to reduce tetrazolium nitro blue as is shown in Example 5. An increase in the number of differentiated cells compared with the control is seen in the treated cultures. Similarly, the treated cells show a reduction in the number of receptors for transferrin, observed by direct immunofluorescence and a much larger number of membrane antigens M01 observed by means of indirect immunofluorescence. The doses of the long chain fatty alcohols of the invention used are of the order of 0.01 to 100 μM, and more particularly 0.1 to 10 μM, in culture. The corresponding doses for in vivo use are of the order of 0.1 to 10 mg/kg.

The use of the derivatives of the invention thus makes it possible to promote the differentiation of cancerous or precancerous cells, in particular the precursors of the macrophages, lymphocytes and monocytes. They enhance in particular their phagocytic and tumoricidal activity.

EXAMPLE 5

CYTOTROPHIC EFFECT ON HL60 LEUKEMIC PROMYELOCYTES.

The use of HL60 leukemic promyelocytes makes it possible to study in vitro their differentiation into monocytes or granulocytes. The HL60 cells are cultures in RPMI medium containing 20% of fetal calf serum; they are inoculated at a density of 3×10⁵ cells per ml and subcultured twice a week (N. Mendelsohn et al. mentioned above). At the time of being placed in culture long chain fatty alcohols of the invention are added at concentrations varying from 0.01 to 100 μM which is used as differentiation signal. After 5 days of culture, a study is made of the differentiation of the HL60 cells into monocytes or into granulocytes which can be measured by morphological changes after staining with May-Grünwald-Giemsa and by their capacity to reduce tetrazolium nitro blue. The undifferentiated cells contain less than 3% of cells capable of reducing this substance. In the cultures treated by the derivatives of the invention, this percentage is significantly increased, whereas the cell volume is appreciably diminished. It is also observed that the intra-cellular medium has become alkaline, which is characteristic of the differentiation into monocytes or into granulocytes.

In order to measure the expression of the receptors for transferrin, a direct immunofluorescence method is used; after the cells have been rinsed, they are incubated with anti-transferrin receptor antibody coupled to fluorescein for 1 h at +4° C. The cell suspension is filtered through a nylon net before being transferred to the cytofluorometer. A reduction in the number of receptors for transferrin is observed from the 2nd day of culture. Subsequently, the expression of phenotypic markers, such as the membrane antigens M02, specific for the monocytes and M01, present on monocytes and granulocytes is studied. The labelling is performed with anti-M01 and anti-M02 antibodies (Coultronics), followed by incubation for 1 h at +4° C. with the anti-mouse rabbit antibody coupled to fluorescein. After 3 days of culture, the percentage of cells expressing M01 increases whereas the expression of M02, specific for the monocytes, appears after 4 or 5 days, when the cultures are maintained in the presence of the long chain fatty alcohols of the invention.

Labelling with propidium iodide shows that the cells accumulate in the G0/G1 phase of the cell cycle. During the differentiation of HL60 cells, an increase in the cAMP-dependent protein kinase activity, an increase in transglutaminase activity and a reduction in the expression of the c-myc oncogene are also observed.

These results show that the long chain fatty alcohols of the invention used at doses varying from 0.01 μM to 100 μM, and more particularly 0.1 to 10 μM, make it possible to induce the differentiation of promyelocytes into granulocytes or monocytes. The cells induced possess the differentiation characteristics of the granulocytes and monocytes, in particular their phagocytic activity, which enables them to play a fundamental role in the protection of the organism against the development of cancerous tumors.

8) Examples of culture media used in combination with the derivatives of the invention.

a) Culture of neuronal cells

Minimum Essentially medium modified by DULBECCO (DMEM) according to DULBECCO, R., FREEMANN G., Virology, 8, (1959) 396, supplemented with:

| transferrin | 100 μg/ml (final concentrations) |
|---|---|
| insulin | 5 μg/ml |
| selenium | 30 nM |
| putrescine | 0.1 mM |
| progesterone | 20 nM |
| hexacosanol | 500 nM | b) Culture of keratinocytes or fibroblasts

Minimum Essential Medium according to EAGLE, H., Science, 130, (1959), 432 supplemented with:

| EGF (epidermal growth factor) | 10 ng/ml |
|---|---|
| hydrocortisone | 0.4 μg/ml |
| hexacosanol | 1 μM | c) Culture of endothelial or mesangial cells

Medium 199 according to MORGAN, J. F., et al., Proc. Soc. Exp. Biol. Med.; 73 (1950), 1:50 Vol %

Medium RPMI 1640 according to MOORE, G. E. et al., J. Am. Med. Assoc., 199, (1967) 519:50 Vol % supplemented with:

| HEPES | 10 mM |
|---|---|
| L-glutamine | 2 mM |
| hexacosanol | 1 μM | d) Culture of hepatocytes

Medium Ham F12 according to HAMM, R. G., Proc. Nat. Acad. Sci., 53 (1965) 288 supplemented with:

| BSA (bovine serum albumin) | 1 g/l |
|---|---|
| insulin | 10 mg/l |
| hexacosanol | 10 μM | e) Culture of mycoplasmas 200 ml of complete medium requires:
140 ml of PPLO medium, containing:

| beef heart proteins | 50 g |
|---|---|
| peptone | 10 g |
| NaCl | 5 g |

(amounts required to prepare 1 l in distilled water)
60 ml of a preparation containing:

| 25% yeast extract | 1 part |
|---|---|
| normal horse serum | 2 parts | supplemented with:

| | |
|---|---|
| 0.4% phenol red | 1.0 ml |
| 50 g of glucose in 100 ml | 4.0 ml |
| penicillin (100,000 μ/ml) | 6.0 ml |
| 10% thallium acetate | 0.5 ml |
| 20 mM hexacosanol | 0.5 ml | f) Culture of lymphocytes and macrophages
Medium RPMI 1640 according to MOORE et al., J. Am. Med. Assoc., 199 (1967) 59 supplemented with:

| | |
|---|---|
| L-alanine | 8.9 mg/l (final concentration) |
| L-asparagine | 15.0 mg/l |
| L-aspartic acid | 13.3 mg/l |
| L-glutamic acid | 14.7 mg/l |
| glycine | 7.5 mg/l |
| L-proline | 11.5 mg/l |
| L-serine | 10.5 mg/l |
| calf serum | 5% |
| hexacosanol | 1 μM |

BRIEF DESCRIPTION OF THE DRAWINGS

The legends to FIGS. 1 and 2 and the figures themselves show.

Figure 1B:
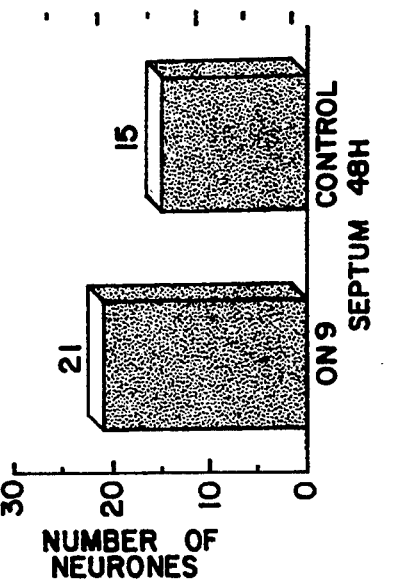
FIGS. 1A–C: increase of neuronal survival in the presence of retinal derivatives (ON13, ON9 and ON8); specific effect on various cerebral regions (cortex, FIG. 1A; suptum, FIG. 1B; hippocampus, FIG. 1C).
Figure 1A:
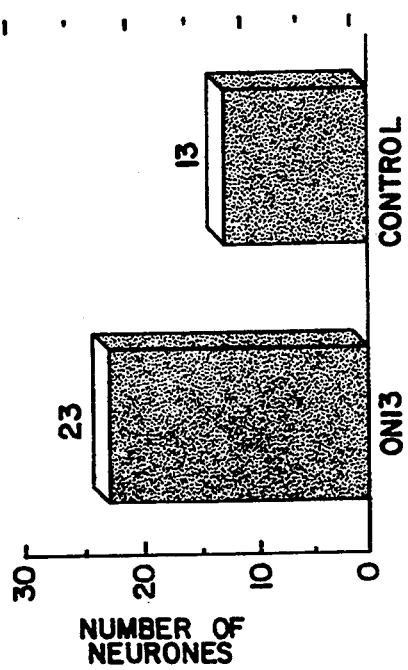
Figure 1C:
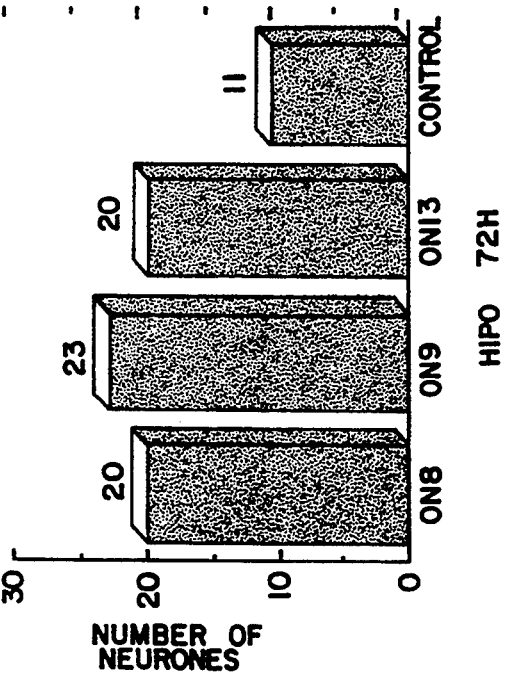
Figure 2:
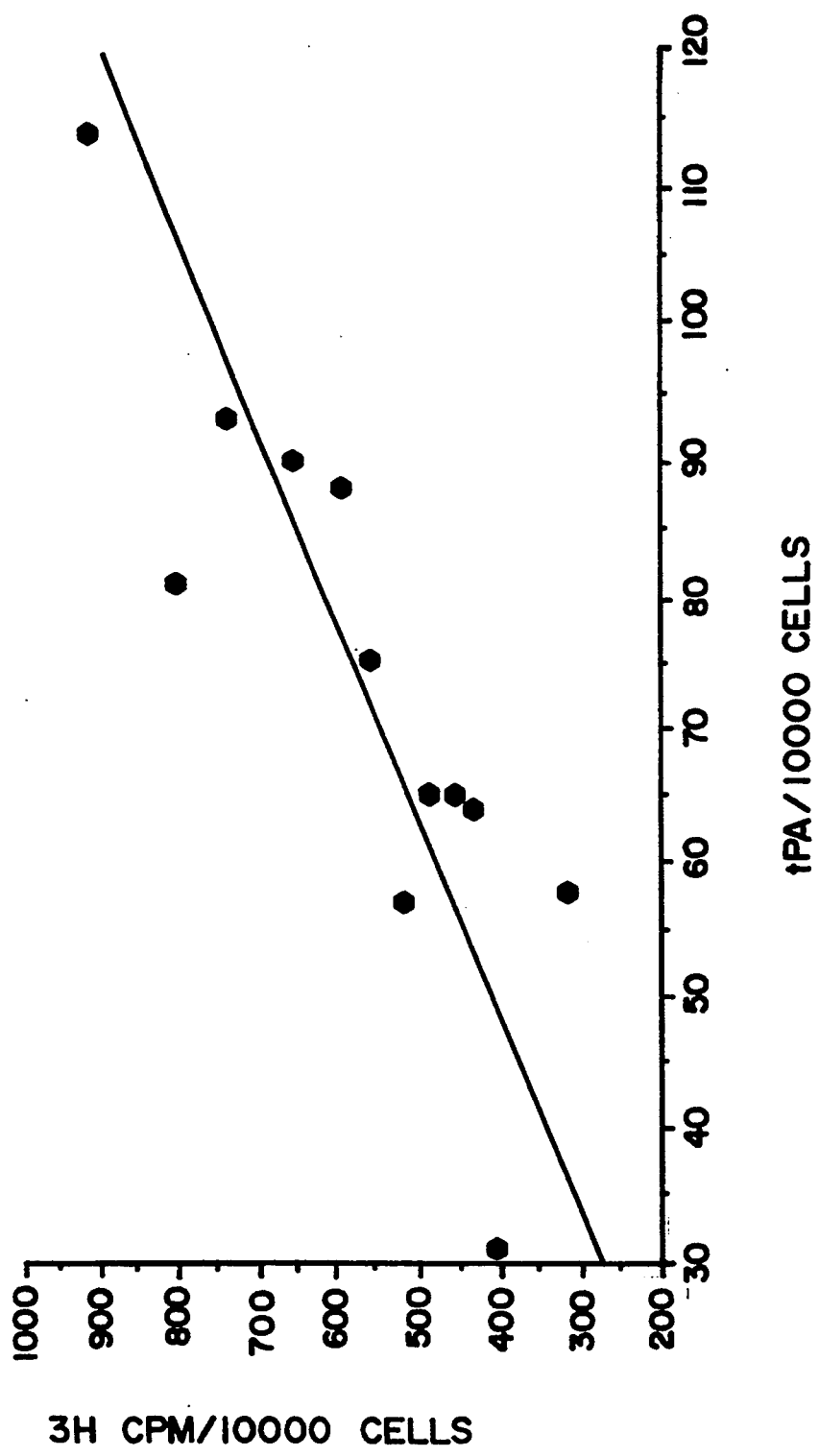
FIG. 2: increase of tPA synthesis (tissue plasminogen activator) by mesangial cells in the presence of n-hexacosanol.

I claim:

1. A method of treating neuronal degradation caused by chemical substances or excitatory amino acids; said method including administering to a mammal in need of said treatment a pharmaceutically acceptable amount of a derivative of the following formula:

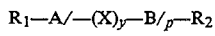

in which
p is equal to 1 or 2,
y = 0 or 1,
A—(X)$_y$—B is a hydrocarbon chain of 11 to 50 carbon atoms, wherein said hydrocarbon chain is unsubstituted or substituted by one or more alkyl groups of 1 to 3 carbon atoms, or by one or more OR$_a$ groups, R$_a$ representing H or an alkyl group of 1 to 3 carbon atoms, in which:

A and B, identical or different, are saturated or unsaturated aliphatic chain;
X is a saturated or unsaturated hydrocarbon chain;
R$_1$ and R$_2$, identical or different, represent:
a group of formula (A):

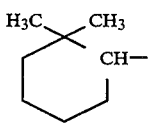

containing a single or a double bond and being unsubstituted or substituted by one or more —CH$_3$ and/or —OH and/or —OR groups, R being defined below, and/or an oxy (=O) group,
a —OR group, in which R represents a hydrogen atom or an alkyl group of 1 to 3 carbon atoms, or a

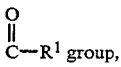

in which R$^1$ represents a hydrogen atom or an alkyl group of 1 to 5 carbon atoms, provided that at least one of the pair of R$_1$ and R$_2$ represent a group of the formula (A).

2. The method according to claim 1, wherein said method comprises treating neuronal degradation caused by chemical substances.

3. The method according to claim 1, wherein said method comprises treating neuronal degradation caused by excitatory amino acids.

4. The method according to claim 1 wherein the derivative is a material according to the formula:

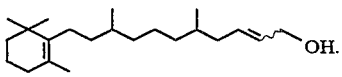

* * * * *

UNITED STATES PATENT AND TRADEMARK OFFICE
CERTIFICATE OF CORRECTION

PATENT NO. : 5,447,959

DATED : September 5, 1995

INVENTOR(S) : Borg

It is certified that error appears in the above-identified patent and that said Letters Patent is hereby corrected as shown below:

```
In column 10, line 45, "CRELYN" should be --CREMLYN--.
In column 12, line 65, "anti-vital" should be --anti-viral--.
In column 16, line 31, "nil" should be --ml--.
In column 23, line 60, "nil" should be --ml--.
In column 20, line 22, insert --TEA:triethylamine-- after
the numeral "(1,50,50)".
In column 20, line 50, "(60/40)" should be --(40/60)--.
In column 22, line 1, insert --24-- after the word "with".
In column 33, line 31, "0.1 to 1yM" should be --0.1 to 1mM--.
In column 34, line 29, "vital" should be --viral--.
In column 38, line 11, "medium" should be --Medium--.
```

Signed and Sealed this

Third Day of September, 1996

*Attest:*

BRUCE LEHMAN

*Attesting Officer*   Commissioner of Patents and Trademarks